United States Patent
Plessala et al.

(10) Patent No.: US 11,478,274 B2
(45) Date of Patent: Oct. 25, 2022

(54) SYSTEM AND METHOD FOR INTRAUTERINE INSEMINATION

(71) Applicant: InnoMed Seven, LLC, Mobile, AL (US)

(72) Inventors: Kirby J. Plessala, Mobile, AL (US); Deneen T. Plessala, Mobile, AL (US); Peter T. Falkner, Mobile, AL (US)

(73) Assignee: InnoMed Seven, LLC, Mobile, AL (US)

( * ) Notice: Subject to any disclaimer, the term of this patent is extended or adjusted under 35 U.S.C. 154(b) by 0 days.

(21) Appl. No.: 17/283,222

(22) PCT Filed: Oct. 10, 2019

(86) PCT No.: PCT/US2019/055688
§ 371 (c)(1),
(2) Date: Apr. 6, 2021

(87) PCT Pub. No.: WO2020/077122
PCT Pub. Date: Apr. 16, 2020

(65) Prior Publication Data
US 2021/0386456 A1    Dec. 16, 2021

Related U.S. Application Data

(63) Continuation-in-part of application No. PCT/US2019/028630, filed on Apr. 23, 2019, and a
(Continued)

(51) Int. Cl.
*A61B 17/43* (2006.01)
*A61B 10/00* (2006.01)

(52) U.S. Cl.
CPC .......... *A61B 17/43* (2013.01); *A61B 10/0012* (2013.01)

(58) Field of Classification Search
CPC ..... A61B 17/43; A61B 17/425; A61B 17/435; A61M 2025/0213; A61M 2025/0293; A61M 25/04
(Continued)

(56) References Cited

U.S. PATENT DOCUMENTS 3,811,443 A * 5/1974 Dickinson, III .......... A61F 6/08
600/35
4,036,212 A * 7/1977 Karuhn .................... C12Q 1/66
436/104
(Continued)

*Primary Examiner* — Samuel G Gilbert
(74) *Attorney, Agent, or Firm* — Intellectual Property Consulting, LLC; Stephen M. Kepper

(57) ABSTRACT

A kit and method for intrauterine insemination is provided. The steps of the method include self-monitoring of a menstrual cycle of a patient by said patient, making an abrasion on the endometrial lining of a uterus of the patient following menstruation by the patient, predicting timing of ovulation by using an ovulation monitoring system or inducing ovulation; preparing sperm for insemination during ovulation by the patient, guiding an intrauterine insemination catheter accompanied by a cervical shield into the patient, depositing a semen sample into the uterine cavity or cervical canal, removing the catheter from the body of the patient while using a holding tool to hold the cervical shield in place at the entrance to the uterine cavity, and leaving the cervical shield in place for a predetermined time period.

12 Claims, 22 Drawing Sheets

Related U.S. Application Data continuation-in-part of application No. PCT/US2018/063100, filed on Nov. 29, 2018.

(60) Provisional application No. 62/743,926, filed on Oct. 10, 2018, provisional application No. 62/814,910, filed on Mar. 7, 2019.

(58) Field of Classification Search
USPC .................................................. 600/33–35
See application file for complete search history.

(56) References Cited

U.S. PATENT DOCUMENTS

| | | | | |
|---|---|---|---|---|
| 4,585,438 A | * | 4/1986 | Makler | A61B 17/42 |
| | | | | 604/106 |
| 4,685,471 A | * | 8/1987 | Regas | A61B 10/0012 |
| | | | | 600/551 |
| 2006/0208055 A1 | * | 9/2006 | Craig | G06C 3/00 |
| | | | | 235/88 RC |
| 2009/0326410 A1 | * | 12/2009 | James | G16H 40/63 |
| | | | | 600/551 |
| 2016/0290913 A1 | * | 10/2016 | Demirci | G01N 15/00 |

* cited by examiner

SYSTEM AND METHOD FOR INTRAUTERINE INSEMINATION

RELATED APPLICATIONS

This application claims priority to U.S. Provisional Patent Application No. 62/743,926, filed Oct. 10, 2018, for "System and Method for Intrauterine Insemination"; PCT Application No. PCT/US19/28630, filed Apr. 23, 2019, for "Device and Method for Improving Implantation of Fertilized Egg During Pregnancy"; U.S. Provisional Patent Application No. 62/814,910, filed Mar. 7, 2019, for "Device and Method for Improving Implantation of Fertilized Egg During Pregnancy"; and PCT Application No. PCT/US18/63100, filed Nov. 29, 2018, for "Device and Method for Artificial Insemination".

FIELD

The present invention relates in general to medical devices and procedures. More specifically, the present invention relates to a kit and method for improving the intrauterine environment prior to and during pregnancy.

BACKGROUND

Intrauterine insemination ("IUI") aims to place sperm into the reproductive system of a patient to promote pregnancy. Typically, IUI is carried out for several reasons, including cervical mucous problems, antisperm antibodies, low sperm concentration, poor sperm mobility in the cervical canal, or simply to increase the number of viable sperm in the uterine cavity. Currently, there are many tools that are utilized in their individual capacity to increase the likelihood of a successful pregnancy using IUI, but heretofore, those tools have not yet been combined in a logical manner to maximize success.

Several clinical prerequisites exist prior to selecting IUI to treat infertility. In general, before initiating an IUI cycle, the treating physician should order a test, such as a hysterosalpingogram (HSG) or a sonohysterosalpingogram (Femvue), for example, to confirm that at least one fallopian tube and the uterus are acceptable for initiating a pregnancy in the female partner. The male partner should undergo evaluation for the quality of the sperm source through semen analysis prior to selecting IUI treatment. Both male and female partners should be appropriately screened for infectious and genetic diseases prior to initiating an IUI cycle. Specific counseling regarding risks of multiple pregnancy and cyst formation should be provided prior to an initiating IUI cycle.

IUI may fail, at least in part, due to a harmful intrauterine environment that prevents a fertilized egg from successfully implanting itself on the wall of the uterus. Accordingly, a physician should utilize all available resources to improve the environment in the uterus prior to insemination. In the past, physicians would intentionally scratch the endometrium layer of the uterus to trigger an inflammatory response within the uterine cavity prior to ovulation. The body's natural wound healing response following the scratch improves the environment of the endometrium and makes it more likely for an embryo to implant and create a pregnancy. Unfortunately, the commonly accepted method for performing this procedure involves the physician blindly pushing the catheter forward until he feels resistance; thereafter, believing he has reached the uterine wall, he would haphazardly begin scratching. This random scratching of the uterine wall is both uncontrolled and operator dependent, which can lead to increased rates of complications such as uterine perforation or damage to the tubal ostia. A new device, known as Accubrade™, has since been developed to solve this problem, which is disclosed in U.S. Provisional Application Nos. 62/662,253, filed Apr. 25, 2018 and 62/814,910, filed Mar. 7, 2019, and PCT Application No. PCT/US19/28630, filed Apr. 23, 2019, entitled "Device and Method for Improving Implantation of Fertilized Egg During Pregnancy," the contents of which are expressly incorporated herein. Unlike predecessor methods, the Accubrade™ device is adapted for controlled insertion into the uterus and further includes a trigger actuated articulating arm that will make a precise, small abrasion on the endometrium wall while avoiding the risk of puncturing or penetrating the uterine wall.

Additionally, for the best chances of a successful pregnancy, it is well known in the art that insemination should take place during ovulation. Accordingly, there are several devices in the art that are used to track ovulation for pregnancy purposes. For example, the Priya Ring™ is a device that monitors cervical temperature to predict the timing of ovulation. Additionally, a physician may use ultrasound monitoring every few days following menstruation to detect follicular development and measure endometrial thickness to project a woman's "fertile window." Ovidrel® may also be used to stimulate follicular release and force ovulation.

Another process that enhances pregnancy chances is to clean and prepare the sperm for fertilization prior to insemination. Common sperm separation procedures, such as the density gradient method, can require multiple rounds of centrifugation. This practice is known to create sperm-damaging reactive oxygen species and DNA fragmentation, which can affect the outcomes of artificial reproductive technology procedures. In order to address these concerns, sperm separation devices that do not require centrifugation have been developed in the art. A device known as ZyMot™ is an example of such a device; any patents, patent applications, or other publications disclosing the ZyMot™ device and method of use for sperm preparation are expressly incorporated herein, including but not limited to International Application No. PCT/US2014/066405, as well as any subsequent applications claiming priority thereto. At a minimum, the ZyMot™ device separates sperm based on motility within a microenvironment created by the micropores in the filter. The device has an inlet port that communicates with the lower sample chamber. The sample chamber is separated from the upper collection chamber by a microporous filter. Untreated semen is added through the inlet port. After a period of time, the separated sperm are collected from the upper chamber through the outlet port. The purpose of ZyMot™ is to separate the most viable, motile sperm in a sample through this gentle filtration process, without iatrogenic damage of sperm and DNA fragmentation.

After the sperm are prepared, the next step is insemination where a semen sample is deposited into a patient's uterine cavity. Generally, during such procedures, a patient's vaginal walls are held open by a medical device, such as a speculum. A semen sample is then inserted into the patient's cervical canal or uterine cavity, depending on which procedure is being performed, typically via a catheter-syringe assembly. After insertion, the semen is deposited into the patient's reproductive system.

However, a portion of the semen sample is often lost by leaking from the cervical canal into the vaginal cavity of the patient due to reflux caused by uterine contractions. Accordingly, unless a barrier is established between the patient's cervical canal and vaginal cavity after the semen sample is inserted, the efficacy of the insemination procedure may be diminished due to such reflux.

In order to prevent such reflux, a shielding device—for example, such as the one described in International Application Nos. PCT/US16/64243, filed Nov. 30, 2016, PCT/US17/64028, filed Nov. 30, 2017, and PCT/US18/63100, filed Nov. 29, 2018, the contents of which are expressly incorporated herein—is often deployed in order to serve as a cervical plug after insemination; the device disclosed in these applications is known in the art as SEMSECURE™. Such shielding devices vary in size and shape, but the general configuration consist of some form of wall or barrier, with a bore usually in the center of the barrier.

An issue with plugs is that they may become dislodged when the catheter is removed. A solution is the use of the catheter, where the catheter is then fed through the bore of the shielding device and inserted into the cervical canal or uterine cavity where a semen sample is directed through the catheter and deposited into the reproductive system. After insemination, the shielding device serves as a barrier between the cervical canal and the vaginal canal. The catheter is subsequently removed, however, the shielding device is held in place by a holding device, such as the device disclosed in U.S. Application No. 62/716,200 and known as SEMSUPPORT™, the contents of which are incorporated herein. Previously, these devices have not been sequenced and organized in a way to maximize the likelihood of a successful pregnancy.

BRIEF SUMMARY OF THE INVENTION

In accordance with embodiments of the invention, a method for intrauterine insemination is provided. The method includes a step (a) of self-monitoring of a menstrual cycle of a patient by the patient. Step (b) of the method makes an abrasion on the endometrial lining of a uterus of the patient following menstruation by the patient. Step (c) of the method (i) predicts timing of ovulation by using an ovulation monitoring system or (ii) induces ovulation. Step (d) of the method prepares sperm for insemination during ovulation by the patient. Step (e) of the method guides an intrauterine insemination catheter accompanied by a cervical shield into the patient. Step (f) of the method deposits a semen sample into the uterine cavity or cervical canal. Step (g) of the method removes the catheter from the body of the patient while using a holding tool to hold the cervical shield in place at the cervical os. Step (h) of the method leaves the cervical shield in place for a predetermined time period.

In one embodiment, the abrasion in step (b) is made using Accubrade™.

In another embodiment, the abrasion in step (b) is made during the pre-ovulatory phase of the menstrual cycle. In one embodiment, the abrasion in step (b) is made during days 7-10 of the menstrual cycle.

In yet another embodiment, the ovulation monitoring system in step (c) uses a Priya Ring™.

In one, embodiment, the ovulatory response will be monitored with traditional urinary LH surge testing.

In one embodiment, the ovulation monitoring system step (c) uses physician-controlled ultrasound monitoring.

In another embodiment, the ovulation in step (c) is induced using Ovidrel®

In yet another embodiment, the sperm for insemination step (d) is prepared using ZyMot™.

In one embodiment, the cervical shield in step (e) is SEMSECURE™.

In another embodiment, the holding tool in step (g) is SEMSUPPORT™.

In yet another embodiment, the predetermined time period in step (h) is between twenty minutes to two hours.

In accordance with embodiments of the invention, a method for intrauterine insemination is provided. The method includes a step (a) of self-monitoring of a menstrual cycle of a patient by said patient. The method includes a step (b) of making an abrasion on the endometrial lining of the uterus following menstruation using Accubrade™ between days 7-10 of the menstrual cycle of the patient. The method includes a step (c) of (i) predicting timing of ovulation using a Priya Ring™ ovulation monitoring system, physician-controlled ultrasound monitoring and/or (ii) inducing ovulation using Ovidrel®. The method includes a step (d) of preparing the sperm for insemination using ZyMot™ during ovulation. The method includes a step (e) of guiding an intrauterine insemination catheter accompanied by a SEMSECURE™ cervical shield into the patient's reproductive system. The method includes a step (f) of depositing a semen sample into the uterine cavity or cervical canal. The method includes a step (g) of removing the catheter from the body of the patient while using a SEMSUPPORT™ holding tool to hold the cervical shield in place at the cervical os. The method includes a step (h) of leaving the cervical shield in place for a period of twenty minutes to two hours.

In accordance with embodiments of the invention, a kit for use in performing an intrauterine insemination is provided. The kit includes an abrasion tool operable for making an abrasion on an endometrial lining of a uterus a patient, an ovulation monitoring tool operable for predicting ovulation of the patient, a sperm treatment tool operable for preparing sperm for insemination into the patient, an intrauterine insemination catheter operable for inseminating the patient with sperm, a cervical shield operable for preventing a semen sample from leaking from a cervical canal into a vaginal cavity of the patient due to reflux caused by contractions of the uterus, and a tool operable for holding the catheter and the cervical shield into the patient.

In one embodiment, the abrasion tool in the kit is Accubrade™.

In another embodiment, the ovulation monitoring tool in the kit is Priya Ring™.

In yet another embodiment, the ovulation inducing tool in the kit is Ovidrel®.

In one embodiment, the sperm treatment tool in the kit is ZyMot™.

In another embodiment, the cervical shield in the kit is SEMSECURE™.

In yet another embodiment, the holding tool in the kit is SEMSUPPORT™.

DETAILED DESCRIPTION

The following applications are hereby incorporated by reference in their entirety: U.S. Provisional Patent Application No. 62/743,926, filed Oct. 10, 2018, for "System and Method for Intrauterine Insemination"; PCT Application No. PCT/US19/28630, filed Apr. 23, 2019, for "Device and Method for Improving Implantation of Fertilized Egg During Pregnancy"; U.S. Provisional Patent Application No. 62/814,910, filed Mar. 7, 2019, for "Device and Method for Improving Implantation of Fertilized Egg During Pregnancy"; U.S. Provisional Application No. 62/662,253, filed Apr. 25, 2018, for "Device and Method for Improving Implantation of Fertilized Egg During Pregnancy"; U.S. Provisional Patent Application No. 62/716,200, filed Aug. 8, 2018, for "Holding Device and Method for Artificial Insemination"; PCT Application No. PCT/US19/45625, filed Aug. 8, 2019, for "Artificial Insemination System and Method of Use"; PCT Application No. PCT/US16/64243, filed Nov. 30, 2016, for "Device and Method for Artificial Insemination"; PCT Application No. PCT/US17/64028, filed Nov. 30, 2017, for "Device and Method for Artificial Insemination"; and PCT Application No. PCT/US18/63100, filed Nov. 29, 2018, for "Device and Method for Artificial Insemination".

Figure 1:
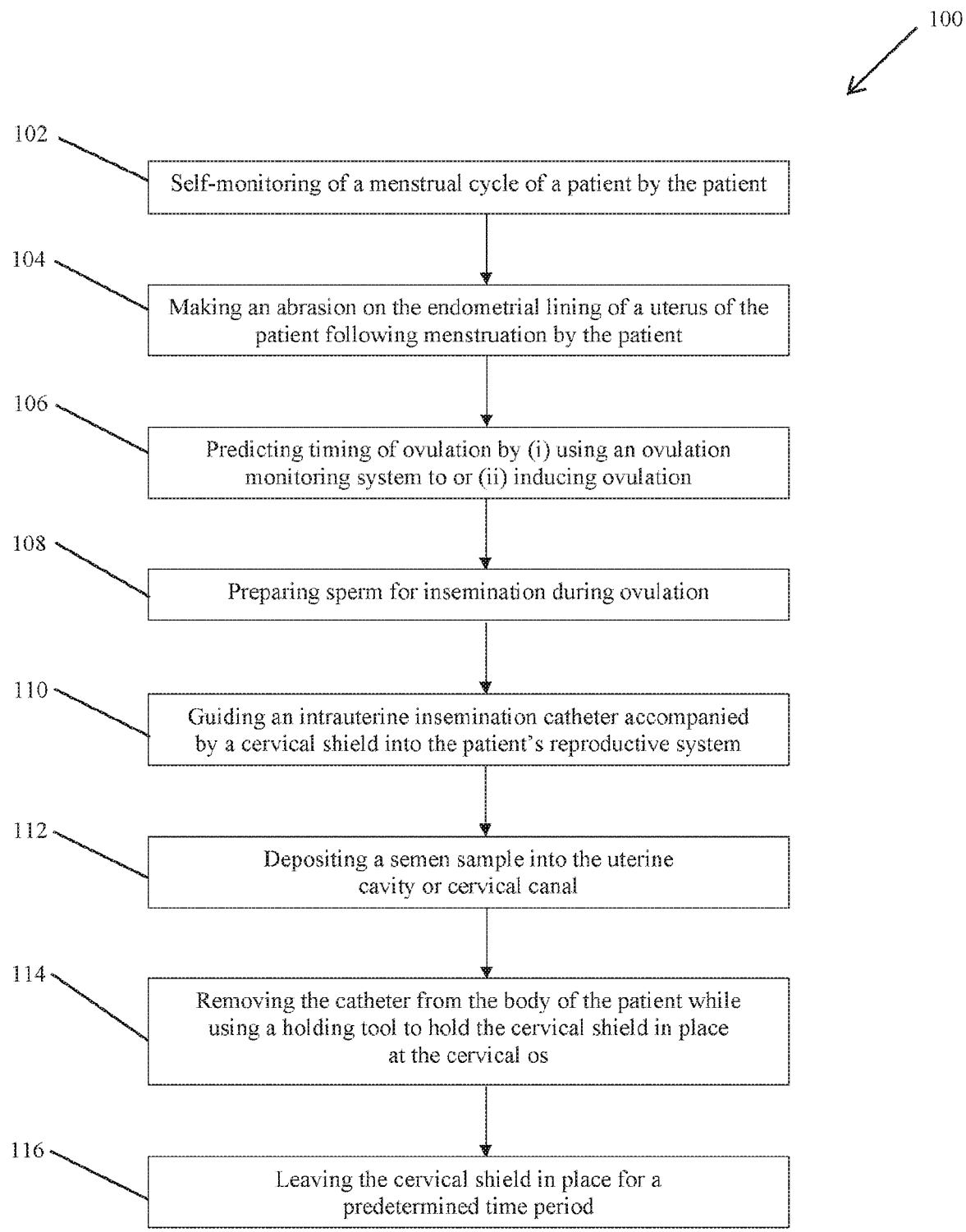
FIG. 1 is a flow diagram showing a preferred method for intrauterine insemination as disclosed.

Referring to the embodiment illustrated in FIG. 1, a method 100 for intrauterine insemination is provided. The method 100 includes a step (a) 102 of self-monitoring of a menstrual cycle of a patient by the patient. Following the completion of menstruation, which should occur on approximately day 6 of the cycle, the patient will go to her physician, preferably between days 7-10 of her menstrual cycle.

In an exemplary situation, a physician will make a precise, tiny abrasion on the endometrial lining of the uterus in step (b) 104 of the method 100. The abrasion in step (b) 104 is preferably made between days 7-9 of the menstrual cycle but at very least a few days prior to ovulation. The preferred device for performing the scratch is the Accubrade™ device as described in U.S. Provisional Application Nos. 62/662, 253, filed Apr. 25, 2018 and 62/814,910, filed Mar. 7, 2019 and PCT Application No. PCT/US19/28630, filed Apr. 23, 2019, entitled "Device and Method for Improving Implantation of Fertilized Egg During Pregnancy," the contents of which are incorporated herein by reference. The Accubrade™ device comprises a handle with a spring loaded trigger and an intravaginal/intracervical/intrauterine arm with an articulating arm at its end that when actuated will move in a bidirectional plane, approximately 4 mm in each direction to give a total moving arc and incision of 1 cm (10 mm) along the endometrial lining of the uterus. The purpose of the device and procedure is to incite an inflammatory reaction in the endometrial cavity which has been shown in the literature to increase the pregnancy success rates of IUI by as much as a factor of 2.0 to 2.3.

After the scratch is performed, the female patient will promptly begin monitoring her reproductive system to predict ovulation. This can be done using a variety of devices and methods known in the art. Step (c) 106 of the method 100 (i) predicts timing of ovulation by using an ovulation monitoring system and/or (ii) inducing ovulation if ovulation has not started. The ovulation monitoring system in step (c) 106 may be without the need of a physician, as the patient may use a device called Priya Ring™, or some other comparable device that utilizes circadian rhythm patterns known as chronobiology to track a female patient's menstrual cycle and accurately predict when ovulation will occur. When the Priya Ring™ notifies the female patient that she is ovulating, IUI should take place within 24 hours. Alternatively, or in combination with the Priya Ring™, a patient's physician may use ultrasound monitoring to detect follicular development and measure endometrial thickness to predict ovulation. Generally, ovulation occurs within days of a mature follicle developing. Preferred indicators for ovulation are a mature follicle of 18 mm or greater and a uterine stripe of 8 mm or greater. If ovulation has not started, the ovulation in step (c) 106 may be induced, at the patient's discretion, by injecting Ovidrel® to stimulate follicular release. Preferably, the injection should take place 24-36 hours prior to IUI. Ovulation should generally occur within 7-10 days of the endometrial abrasion, depending on the patient's menstrual cycle.

Based on the foregoing indicators of ovulation, the patient will promptly see her physician, preferably within twenty-four hours, to undergo IUI while ovulating. At the physician's office and prior to insemination, the sperm must be prepared for fertilization. Step (d) 108 of the method 100 prepares sperm for insemination during ovulation by the patient. The preferred method avoids using a well-known process known as centrifugation to separate sperm, as this process damages the sperm and has led to negative outcomes. Sperm for insemination step (d) 108 may be prepared using a device known in the art used to prepare motile sperm for intrauterine insemination, such as ZyMot™, for example. The ZyMot™ device and method for separating sperm using said device, as well as any patents or patent applications relating thereto, including International Application No. PCT/US2014/066405 are incorporated herein by reference.

After the sperm are prepared, the physician will utilize a catheter to inseminate the uterine cavity. Step (e) 110 of the method 100 guides an intrauterine insemination catheter accompanied by a cervical shield into the patient. During the insertion process, the catheter in step (e) 110 may be is equipped with a cervical plug, such as the SEMSECURE™ device described in International Application Nos. PCT/US16/64243, filed Nov. 30, 2016, PCT/US17/64028, filed Nov. 30, 2017, and PCT/US18/63100, filed Nov. 29, 2018, the contents of which are incorporated by reference. In general, the plugging device has a concave surface that sits flush with the cervix, along with a graduated shaft with a bulb at its tip that secures itself within the cervical canal. The device can come in multiple sizes to ensure an appropriate fit and accommodate for anatomic variations between patients. The proximal portion (the portion that lies outside of the cervical canal) is small enough that any cervical anteversion or retroversion of the uterus will not dislodge the device. There is a central lumen or bore within the middle of the device that allows for the passage of an intrauterine catheter.

Step (f) 112 deposits a semen sample into the uterine cavity or cervical canal. Step (g) 114 of the method 100 removes the catheter from the body of the patient while using a positioning tool to hold the cervical shield in place at the entrance to the uterine cavity. The positioning tool (e.g. SEMSUPPORT™) provides the opposing force against the cervical plug required to keep the plug in place while the catheter is removed through the bore of the plug. Step (h) 116 of the method 100 leaves the cervical shield in place for a predetermined time period while acting as a seal to the passageway from the uterine cavity into the cervical canal. The predetermined time period in step (h) 116 may be between twenty minutes to two hours, for example.

Figure 2:
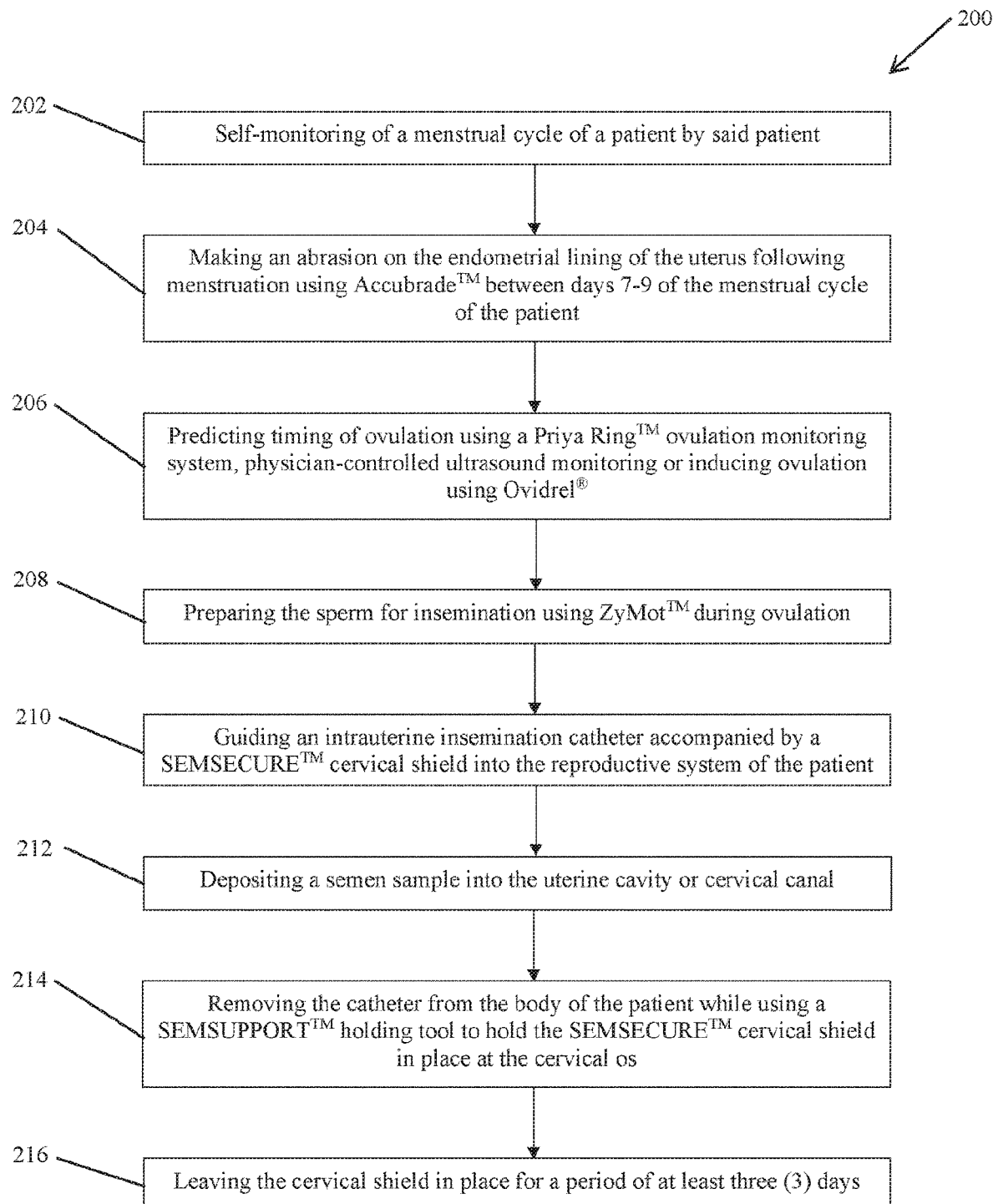
FIG. 2 is a flow diagram showing a preferred method for intrauterine insemination as disclosed.

Referring to FIG. 2, in accordance with embodiments of the invention, a method 200 for intrauterine insemination is provided. The method includes a step (a) 202 of self-monitoring of a menstrual cycle of a patient by the patient. The method includes a step (b) 204 of making an abrasion on the endometrial lining of the uterus following menstruation using Accubrade™ between days 7-9 of the menstrual cycle of the patient. The method includes a step (c) 206 of predicting timing of ovulation using a Priya Ring™ ovulation monitoring system, physician-controlled ultrasound monitoring or inducing ovulation using Ovidrel®. The method includes a step (d) 208 of preparing the sperm for insemination using ZyMot™ during ovulation. The method includes a step (e) 210 of guiding an intrauterine insemination catheter accompanied by a SEMSECURE™ cervical shield into the patient's reproductive system. The method includes a step (f) 212 of depositing a semen sample into the uterine cavity or cervical canal. The method includes a step (g) 214 of removing the catheter from the body of the patient while using a SEMSUPPORT™ holding tool to hold the cervical shield in place at the cervical os. The method includes a step (h) 216 of leaving the cervical shield in place for a period of twenty minutes to two hours.

For the purposes of this patent application, an exemplary kit is defined as comprising an abrasion tool operable for making an abrasion on an endometrial lining of a uterus a patient; an ovulation monitoring tool operable for predicting ovulation of the patient; a sperm treatment tool operable for preparing sperm for insemination into the patient; an intrauterine insemination catheter operable for inseminating the patient with sperm; a cervical shield operable for preventing a semen sample from leaking from a cervical canal into a vaginal cavity of the patient due to reflux caused by contractions of the uterus; and a tool operable for holding the catheter and the cervical shield into the patient.

In accordance with embodiments of the invention, a kit for use in performing an intrauterine insemination is provided. The kit includes an abrasion tool 302 operable for making an abrasion on an endometrial lining of a uterus a patient, an ovulation monitoring tool 800 operable for predicting ovulation of the patient, a sperm treatment tool 810 operable for preparing sperm for insemination into the patient, an intrauterine insemination catheter 753 operable for inseminating the patient with sperm, a cervical shield 690 operable for preventing a semen sample from leaking from a cervical canal into a vaginal cavity of the patient due to reflux caused by contractions of the uterus, and a tool 605 operable for holding the catheter and the cervical shield while in the patient.

Figure 3:
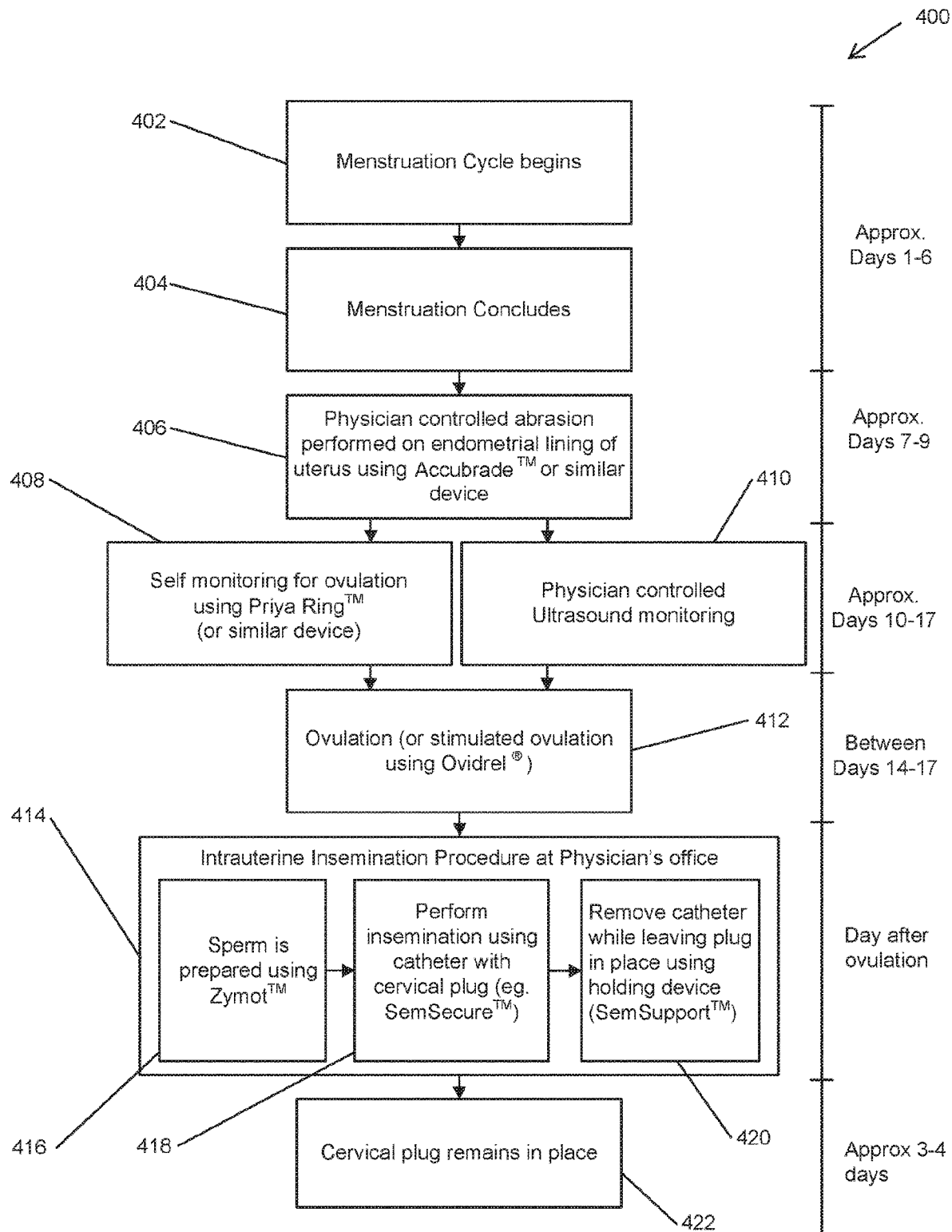
FIG. 3 is a flow diagram showing a preferred method for intrauterine insemination as disclosed.

A method 400 of intrauterine insemination is disclosed in FIG. 3. A patient's menstrual cycle begins in step 402. The menstruation concludes in step 404. In step 406, physician-controlled abrasion is performed on the endometrial lining of the patient's uterus using Accubrade™ or a similar abrasion device known in the art. In step 408, the patient self-monitors for ovulation using Priya Ring™ or a similar ovulation monitoring device known in the art. In step 410, which may coincide with step 408, a physician-controlled ultrasound monitoring occurs. In step 412, the patient ovulates or ovulates after stimulation using Ovidrel®. Step 414 is an intrauterine insemination procedure at a physician's office. Step 414 includes step 416 of preparing sperm using Zymot™, step 418 of performing insemination using a catheter with a cervical plug such as SEMSECURE™, and step 420 of removing the catheter while leaving the plug in place using a holding device such as SEMSUPPORT™. The cervical plug remains in place in step 422.

Figure 4:
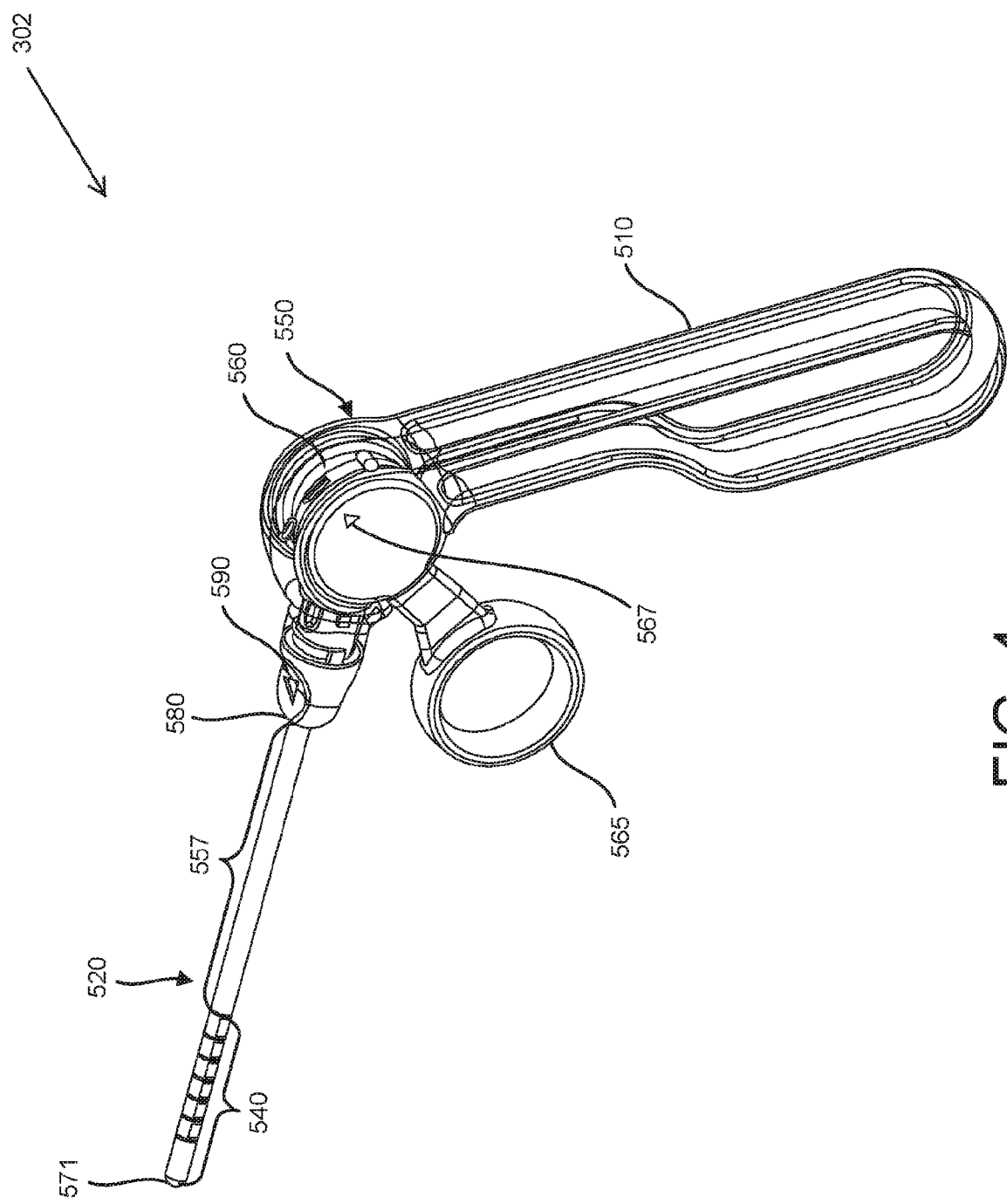
FIG. 4 illustrates an abrasion device in accordance with embodiments of the disclosed invention.
Figure 5:
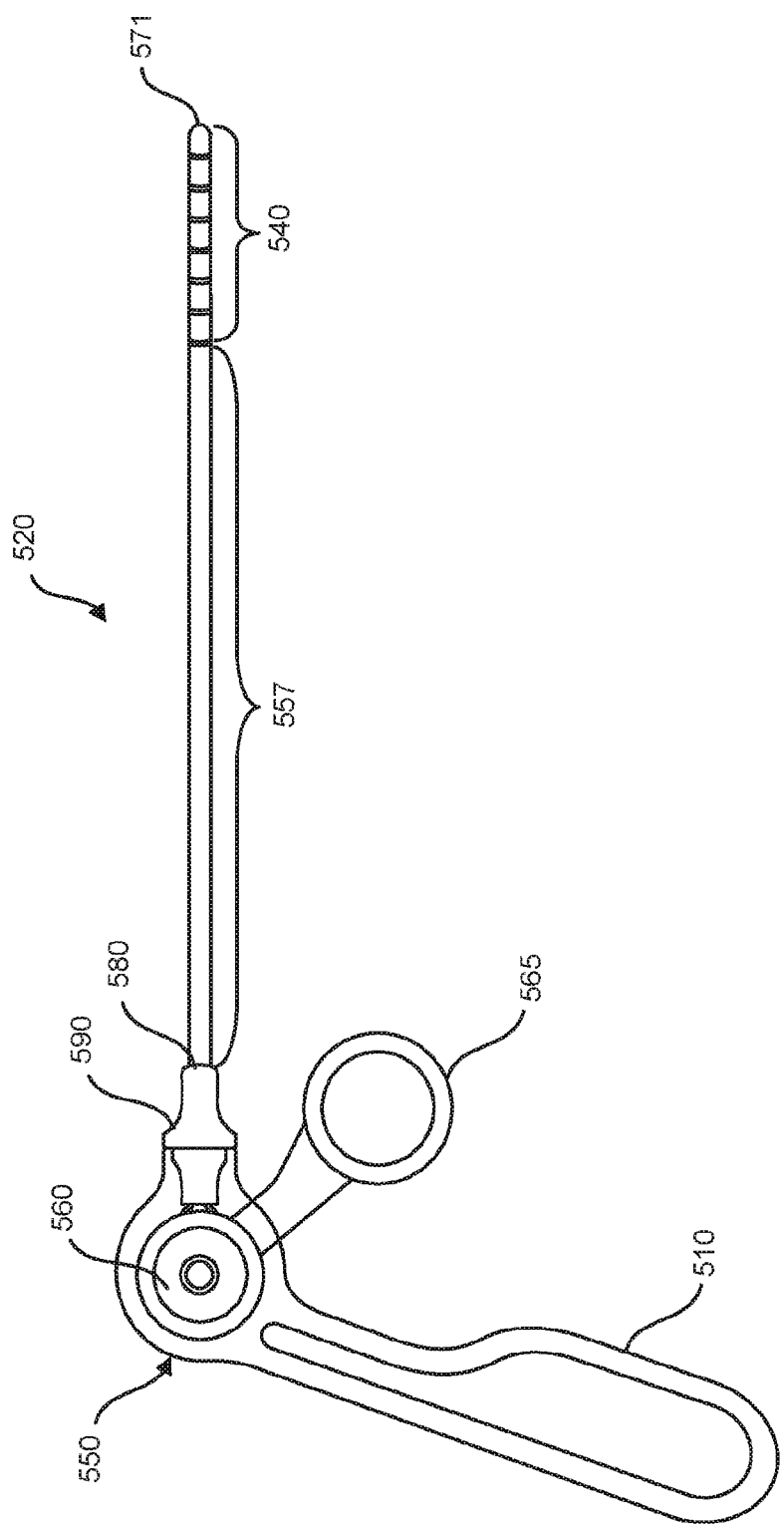
FIG. 5 is a profile view of an abrasion device showing the opposite side from that depicted in FIG. 4.
Figure 6:
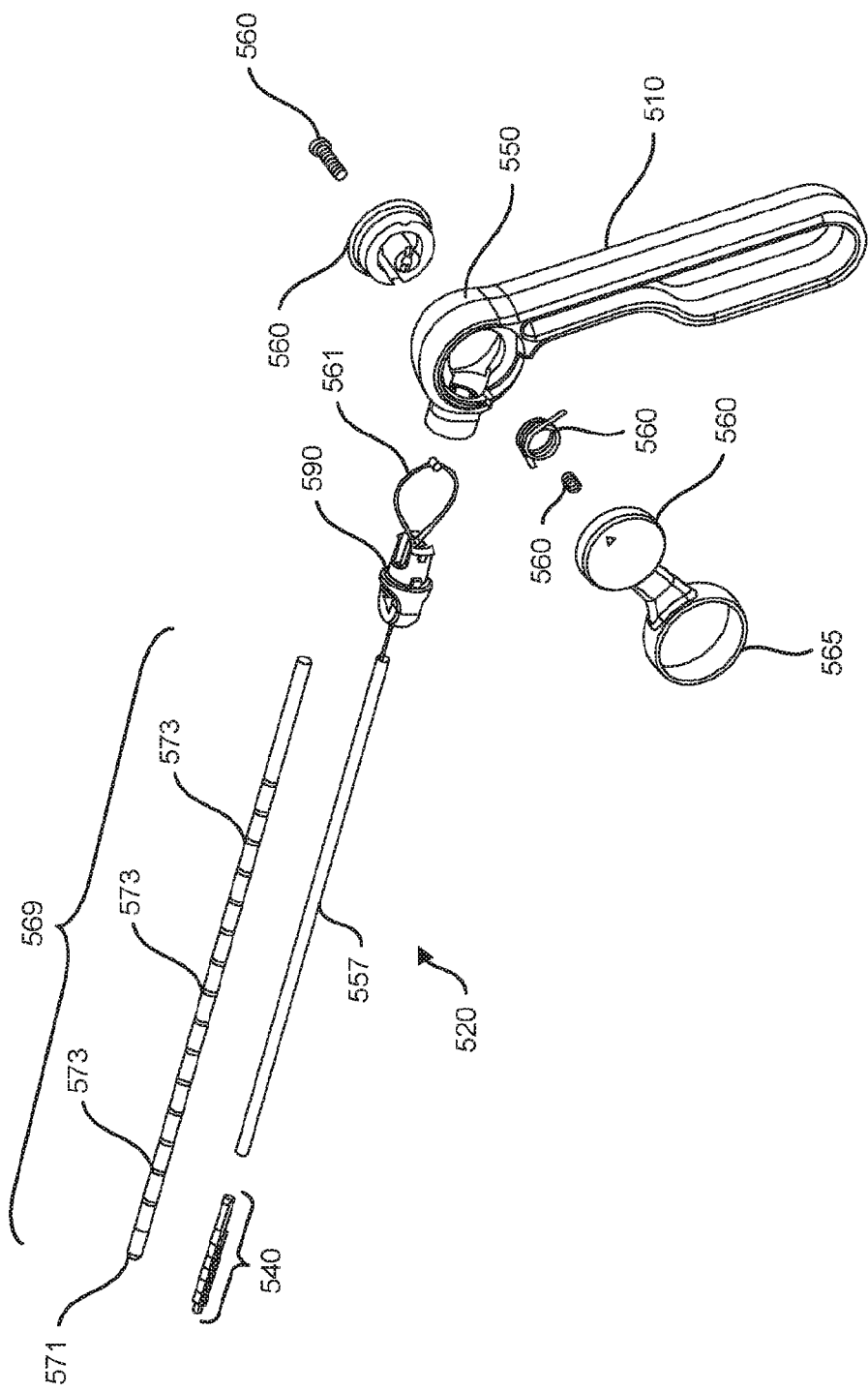
FIG. 6 is an exploded view of an abrasion device.

Turning to FIGS. 4-6, the preferred embodiment of the abrasion tool 302 is Accubrade™, which comprises a handle 510, an arm 520 comprising an articulating tip 540, wherein the handle 510 is connected to the arm 520 by a connection member 550 that contains a spring-loaded trigger mechanism 560 operable to curl the articulating tip 540 in a variety of planar directions by pulling a trigger 565. Preferably, the handle 510 is offset approximately 45° from the longitudinal plane of the arm 520 to allow for easier guidance of the arm 520 into the uterine cavity, and said handle 510 is positioned such that the index finger (not shown) of the user can easily actuate the trigger 565.

Figure 7:
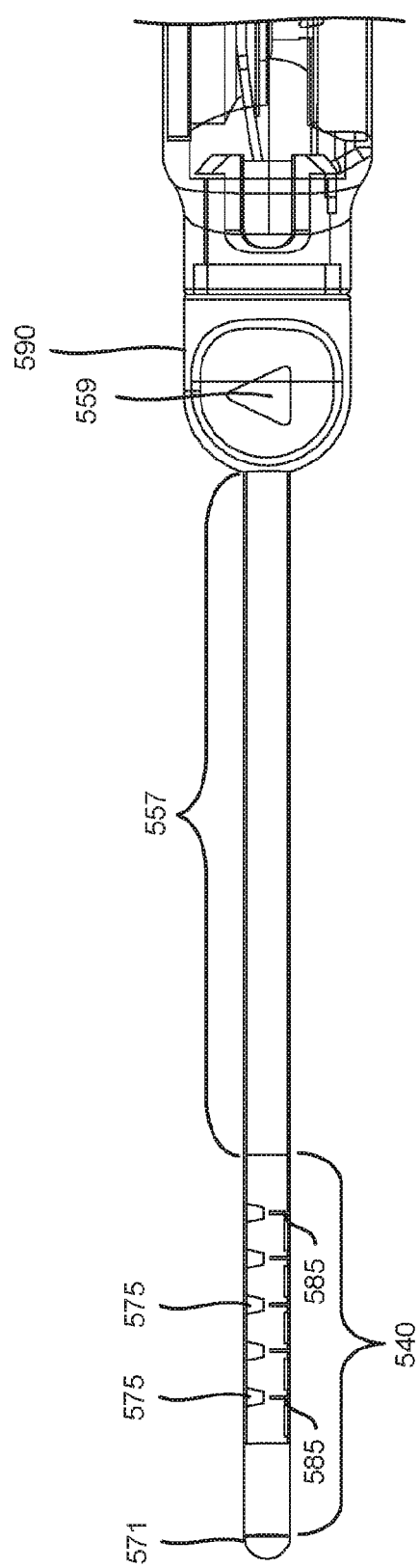
FIG. 7 is a topside view of the arm of an abrasion device.
Figure 9:
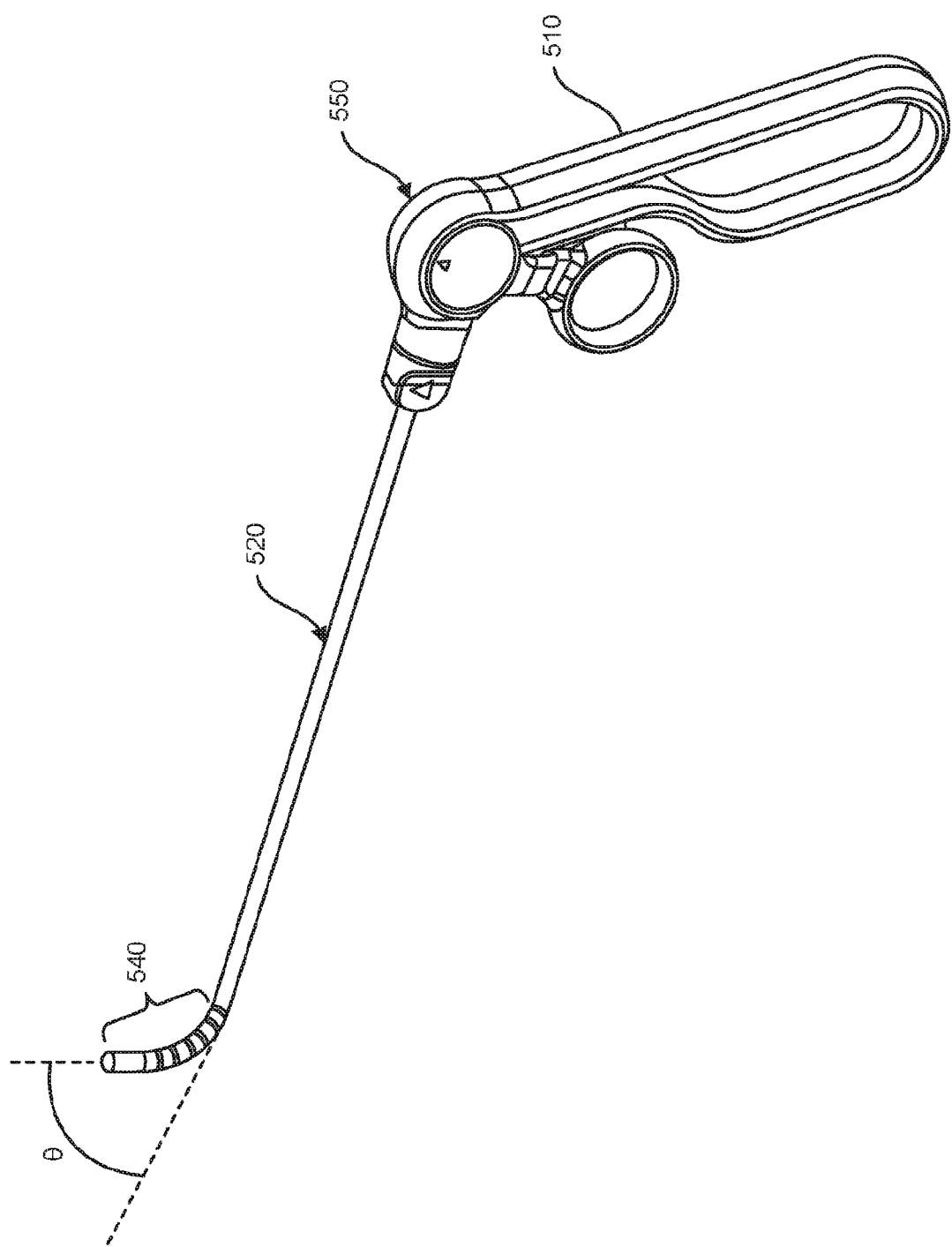
FIG. 9 is a perspective view of an abrasion device showing the articulating tip in a curled position.

Turning to FIG. 7, the articulating tip 540 at the distal end of the arm 520 is made from a material having flexible properties, including but not limited to, flexible polymers, solid foam, thermoplastics, thermoset materials, or other materials known in the art with similar properties. When activated the articulating tip 540 will curl in a given planar direction wherein the inner portion of the curled tip 540 will be compressed and the outer portion of the curled tip 540 will be in tension (as shown in FIG. 9). Accordingly, it is preferable that the articulating tip 540 shall have larger circumferential slits 575 on the inner portion of the tip 540 and smaller circumferential slits 585 on the outer portion of the tip 540 to allow the articulating tip 540 to curl.

The proximal end of the arm comprises a rotatable knob 590 that is operable to adjust the planar direction of the articulating tip 540. The non-flexible portion 557, or rigid portion of the arm 520 positioned between the rotatable knob 590 and the articulating tip 540, is made from a substantially rigid material, e.g. metals or hardened polymers (e.g. carbon fiber or other plastics), to prevent flexion along that portion 557 of the arm 520. For the preferred embodiment, the rotatable knob 590 comprises an indicator, e.g. an arrow 559, which alerts the user as to the planar direction the articulating tip 540 shall curl.

Figure 8:
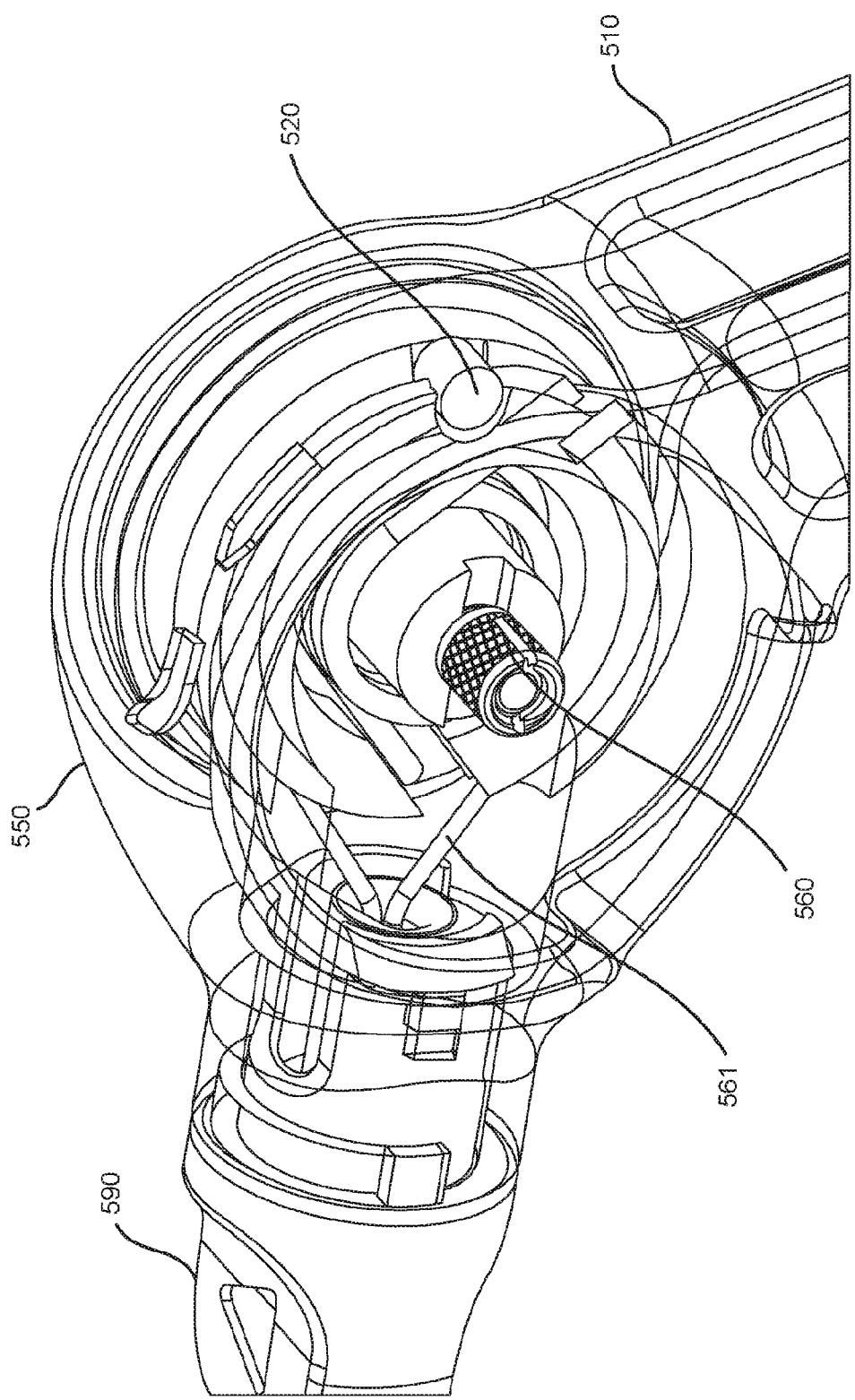
FIG. 8 is a transparent perspective view of the connecting member of an abrasion device showing the trigger mechanism.

As shown in the figures, a cable or wire 561 extends longitudinally from the distal end of the arm 520 and wraps around the spring-loaded trigger mechanism 560 before returning to the distal end of the arm 520 such that a continuous closed loop is formed; a portion of the cable 561 is fixedly attached to the trigger mechanism 560 by a slot-pin 563 (as shown in detail in FIG. 8) or some other attachment means known in the art. Alternatively, the invention anticipates using at least two separate cables or wires 561 that follow a similar path and are in parallel, where one end of the wire is fixedly attached to the trigger mechanism 560 and the opposite end of each wire 561 is fixedly attached at the distal end of the arm 520. For either arrangement, when the trigger 565 is actuated, the trigger mechanism 560 causes one portion of the cable 561 in the arm 520 to slack while the other portion is pulled in tension. This process enables the flexible articulating tip 540 to curl in the direction that the cable 561 is being pulled, thus creating the annular curve θ (as shown in FIG. 6). The degree of annular curve θ created by the articulating tip 540 is directly proportionate to the degree the trigger 565 is pulled towards the handle 510. As shown in the figures, the exterior surface of the trigger mechanism 560 has an arrow 567, which will rotate in an opposite direction of the handle 510 when pulled. As a means to alert the user as to the degree of annular curve θ, the arrow 567 will correspond to measurement markings on the exterior housing (not shown) of the connecting member 550.

Turning to FIGS. 6-7, the preferred embodiment further comprises a sleeve 569 that is adapted to fit over and fully enclose the arm 520; a cap portion 571 of the sleeve 569 covers the distal end of the articulating tip 540. The sleeve may be made from any fabric, polymer, or other material that is flexible and has properties that will either minimize or not cause irritation to the patient. As shown in FIG. 7, the preferred embodiment of the cap portion 571 comprises a rounded surface to further minimize irritation to the patient when in contact with the endometrium layer of the uterus. Although this embodiment is preferred, it is envisioned that the cap portion 571 may come in different sizes, shapes, and materials depending on the needs of the user.

As shown in FIG. 6, it is another aspect of this invention that the exterior surface of the sleeve 569 contain measurement markings 573 that operate to inform the physician of the length of the arm 520 that has been inserted into the patient. Although not required, it is preferred that these markings be spaced apart in one-centimeter increments.

The subject device is to be deployed inside the uterus in order to perform a small, precise abrasion along the endometrium layer of the uterus. For optimal results, the procedure will take place in the days leading up to ovulation; often, this occurs on day 7, 8, or 9 of a menstrual cycle, depending on the patient. Using the handle 510, the physician shall guide the arm 520 through the cervix and into the uterine cavity of the patient until the cap portion 571 of the articulating tip 540 abuts the endometrial lining of the uterus. Next, when the trigger mechanism 560 is actuated by pulling the trigger 565 a distance inward toward the handle 510, the articulating tip 540 will curl in the planar direction as set by the rotating knob 590 and at an angular distance θ proportionate to the degree the trigger 565 is pulled. The articulating tip 540 will create a small abrasion on the lining of the uterus. After the abrasion is made, when the handle 510 is slowly released, the spring-loaded trigger mechanism 560 operates to bring the articulating tip 540 back to its resting state, which is a state of longitudinal alignment with the rigid portion 557 of the arm 520. At this stage, the arm 520 can be safely and easily manually removed from the uterine cavity by the physician.

Figure 10:
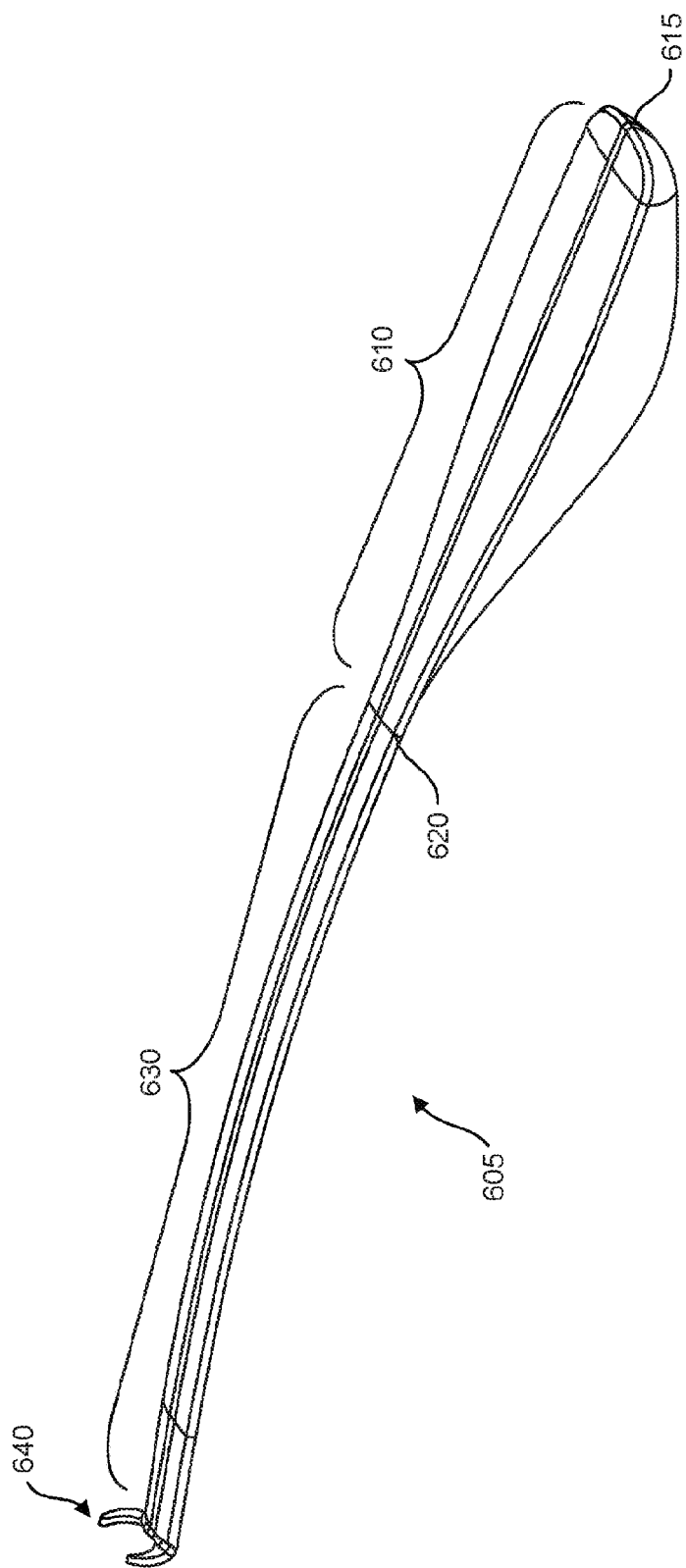
FIG. 10 is a perspective view showing a holding tool.
Figure 11:
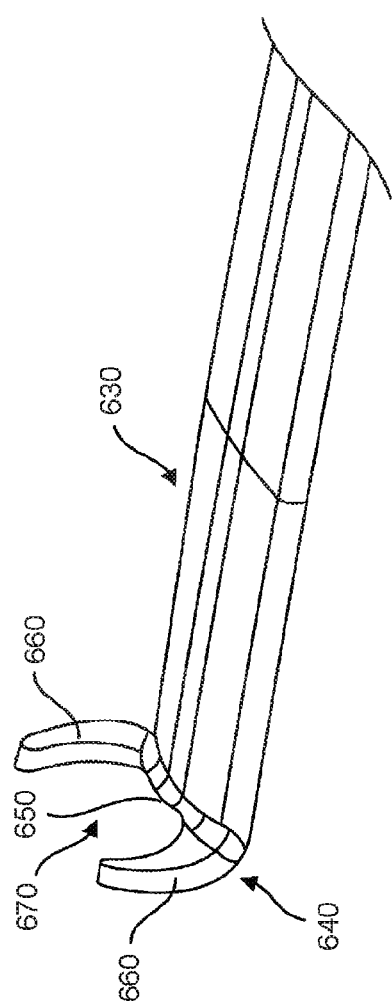
FIG. 11 is a focused perspective view showing the distal end of a positioning tool.

Turning to FIG. 10, a perspective view of the preferred positioning tool 605, SEMSUPPORT™, is shown. The tool 605 generally comprises a handle 610 on one end having a proximal end 615 and a distal end 620, a stem 630 extending longitudinally therefrom and connecting to a bracket 640 at the other end of the tool 605. It is anticipated that the stem 630 can be manipulated to be curved as shown in FIG. 10, or alternatively, may take on other alignments, including but not limited to, a linear alignment. It is envisioned that the positioning tool 605, including the handle 610, stem 630, and bracket 640 are made from a rigid or semi-rigid material (e.g. medical-grade silicone rubber, metal, plastic, glass); however, any part thereof or the entire tool 605 may be made from a flexible material to better assist in the guiding and placement of the tool 605 within the patient's reproductive system. Turning to FIG. 11, the bracket 640 structurally comprises a bottom segment 650 that extends a general horizontal direction with two opposing and spaced apart segments 660 that originate at the bottom segment 650 and extend in a general vertical direction therefrom such the interior of the bracket is accessible through the opening 670 between the opposing segments 660. It is anticipated that the two opposing segments may be linear or curvilinear.

Figure 12:
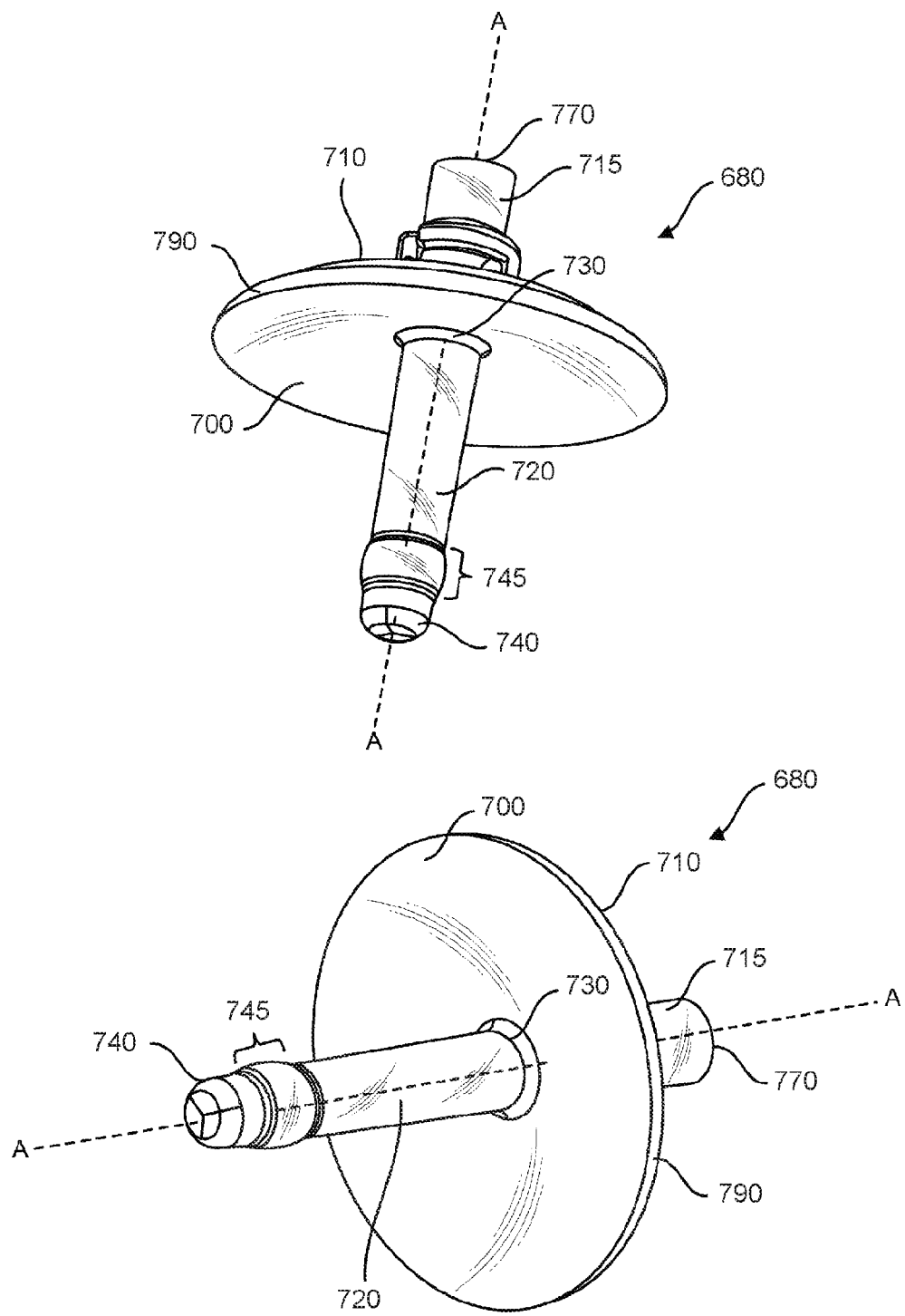
FIG. 12 includes multiple perspective views of a cervical plug showing the valve in the closed position.
Figure 19:
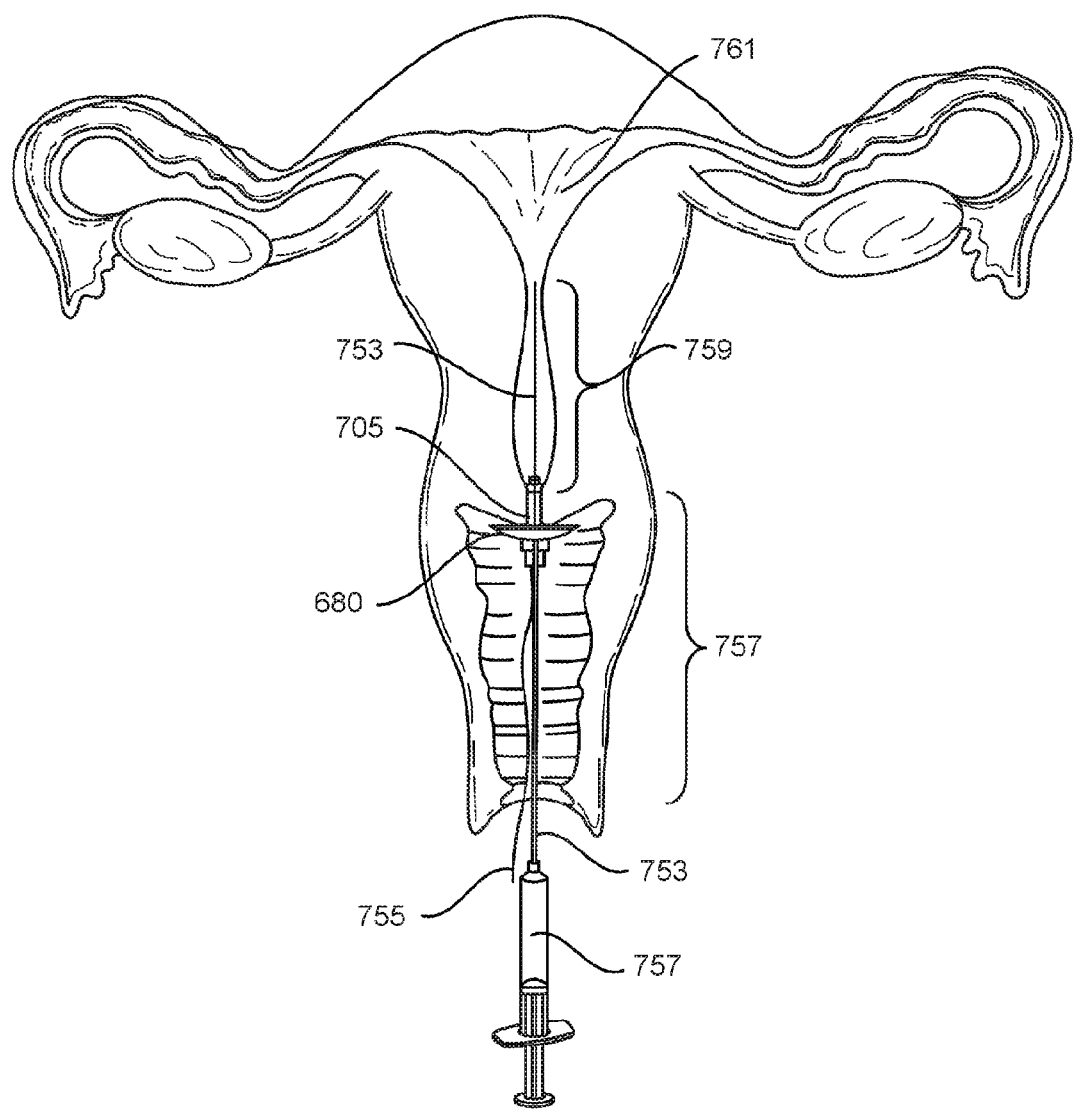
FIG. 19 is a perspective view of the kit within a patient's reproductive system before the positioning tool is inserted.
Figure 20:
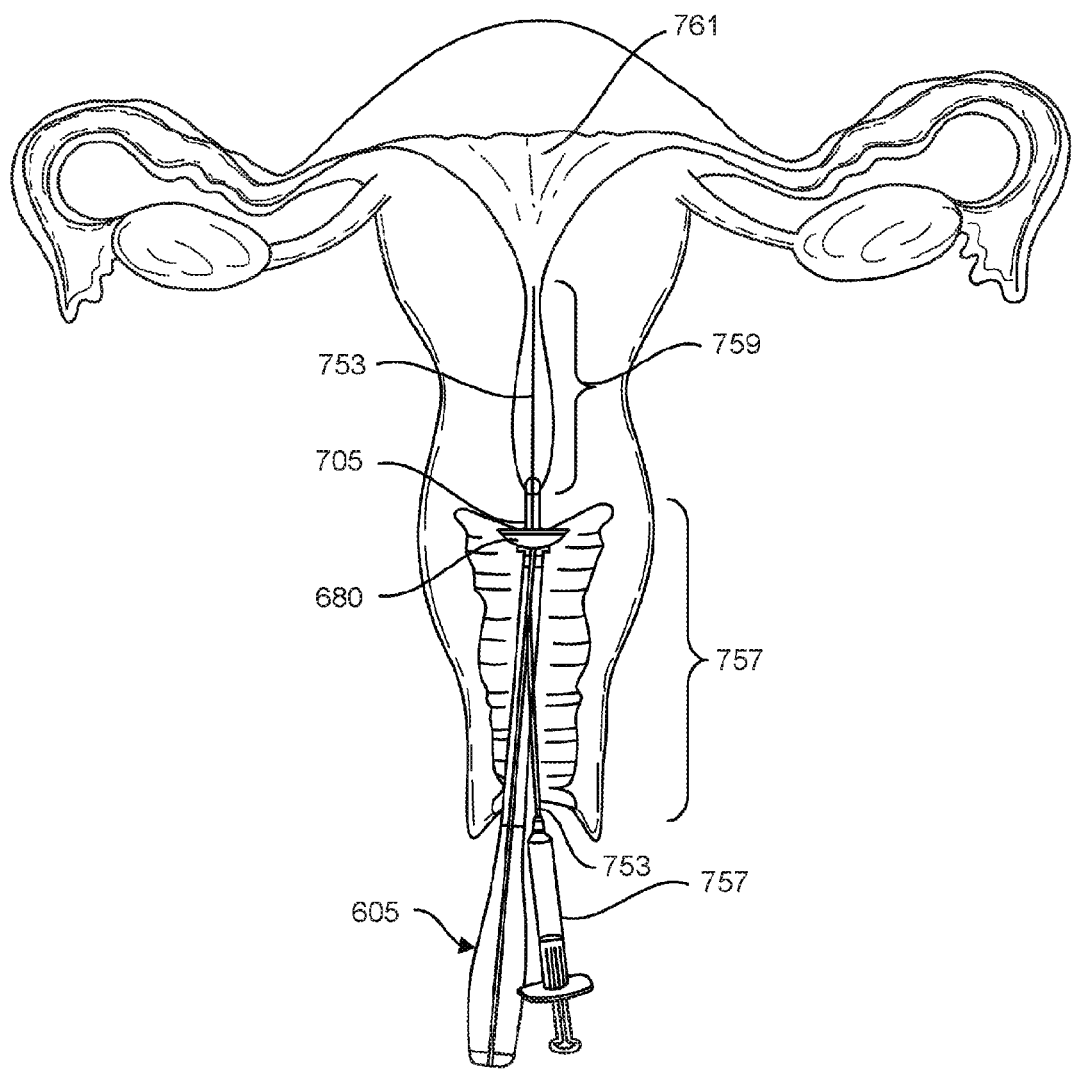
FIG. 20 is a perspective view of the system within a patient's reproductive system.

Turning to FIG. 12, the preferred embodiment for the preferred cervical plug 680, SEMSECURE™, is shown. The cervical plug 680 comprises a shield 690 having a first surface 700 and opposing second surface 710. As shown in the figure, the first surface 700 is preferably concave, but may be any shape to operably cover the cervical os 705 of a patient (as shown in FIGS. 19-20). Alternatively, the shield 690 may be of another shape suitable for covering the cervical os 705 of a patient, such as an elliptical shape. The shield 690 may be shaped and sized such that the shield 690 can cover the cervical os 705 of nulliparous, primiparous, or multiparous women. To minimize pain or discomfort experienced by a patient as the cervical plug 680 is inserted or removed from the patient's body, the shield 690 may be made of a material that is somewhat flexible such that the material may be deformed by pressure applied by a user of the device but return to its original shape when the pressure is removed. Alternatively, the shield 690 may be made of a material that is substantially rigid or semi-rigid. In addition, the shield 690 may be made of a material that is at least partially translucent or transparent, which may aid a user in inserting the device in the cervical canal.

Alternatively, the shield 690 may be made of an opaque material. The shield 90 may comprise medical-grade silicone rubber. Alternatively, the shield 690 may be made of any suitable material including, but not limited to, plastic, glass, ceramic, metal, any type of rubber, or any combination thereof.

The cervical plug 680 further comprises an arm 720 that attaches to the first surface 700 of the shield 690 at the arm's 720 proximal end 730; the distal end 740 of the arm 720 is operable to extend into the cervical os of a patient and may be conically shaped or substantially cylindrically shaped to ease discomfort caused by the insertion of the arm 720 into the patient. The arm 720 is sufficiently rigid for inserting the arm 720 into the cervical canal 759 of a patient (as shown in FIGS. 19-20), but the arm 720 may have some amount of flexibility in order to minimize pain or discomfort experienced by the patient as the cervical plug 680 is inserted or removed. Alternatively, the arm 720 may be made of a material that is substantially rigid. In addition, the arm 720 may be made of a material that is at least partially translucent or transparent. Alternatively, the arm 720 may be made of an opaque material. The arm 720 may comprise medical-grade silicone rubber. However, the arm may be made of any suitable material including, but not limited to, plastic, glass, ceramic, metal, any type of rubber, or any combination thereof.

The arm 720 may have a circumferential bulge 745 to help keep the cervical plug 680 in place with the arm 720 inserted into the cervical canal 759 during use. The bulge 745 is positioned along a length of the arm 720, preferably midway between the proximal end 730 and the distal end 740). Once the arm 720 is inserted into the cervical canal 759, as shown in FIGS. 19-20, the wider diameter of the circumferential bulge 745 provides resistance to removal of the arm 720 from the cervical canal 759, thereby helping to keep the cervical plug 680 in place for a period of time after semen has been introduced into the cervical canal 759 or uterine cavity 761 so that the plug 680 prevents leakage of semen from the cervical canal 759 into the vaginal canal 757. The bulge 745 preferably comprises a contoured surface to prevent discomfort, however, this patent envisions the bulge 745 having other configurations operable to prevent the cervical plug 680 from becoming dislodged.

The arm 720 may be permanently secured to the shield 680. For instance, the arm 720 and shield 690 may be molded as a unitary piece of material. Alternatively, the arm 720 may be secured to the shield 690 with an adhesive. A bore extends longitudinally through the center of the cervical plug 680 with one opening at the proximal end 770 of the insert member 715 and another opening at the distal end 740 of the arm 720; the bore is operable to receive a catheter along the directionally dashed line A through the cervical plug 680.

Figure 13:
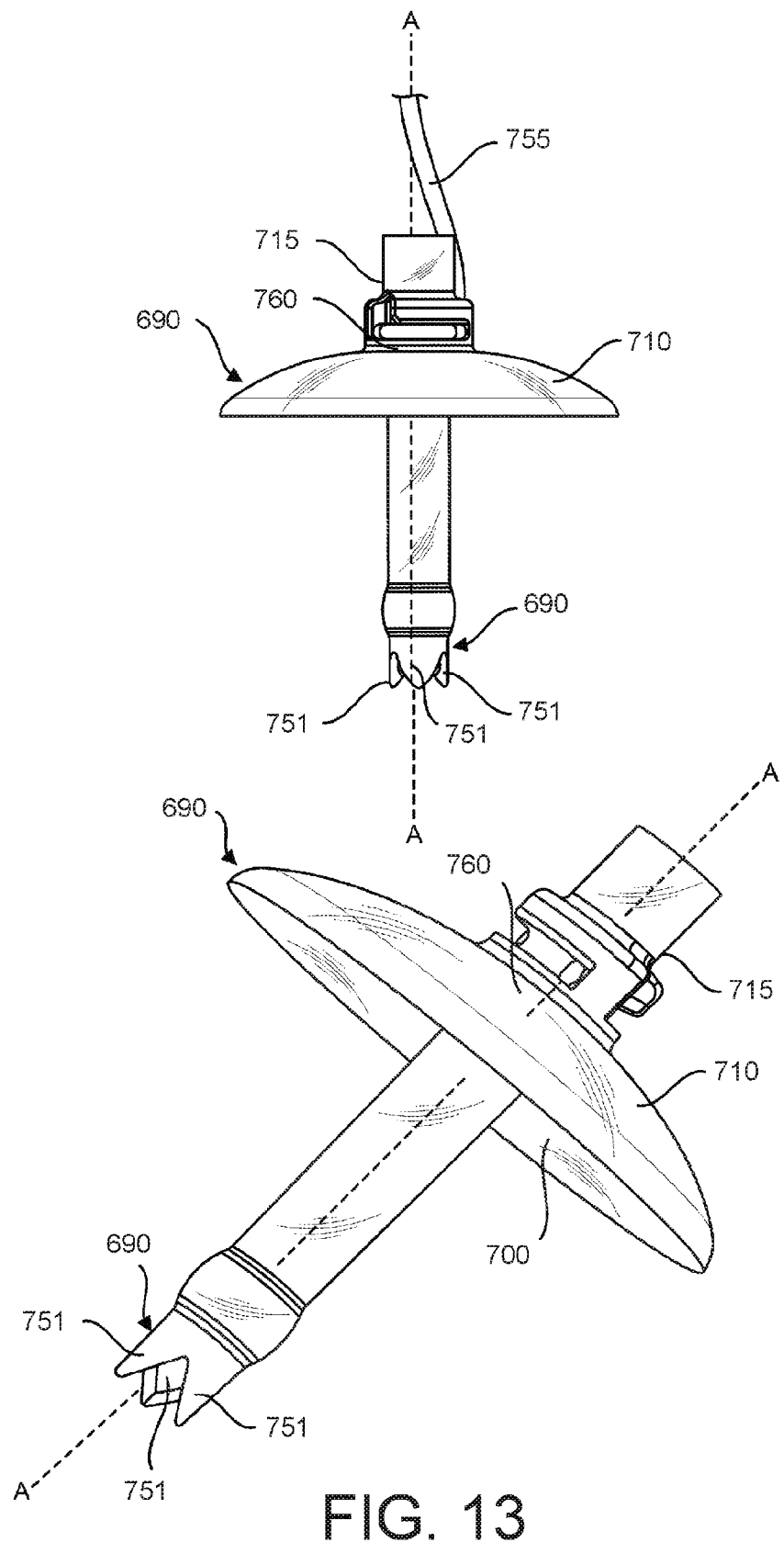
FIG. 13 includes alternative views of a cervical plug with the valve in the open position.

Turning to FIGS. 12 and 13, the distal end 740 of the arm 720 is shown with an optional valve 790 that is operable between an open position (as shown in FIG. 13) and the closed position (as shown in FIG. 12). The valve 790 further comprises elastomeric flaps 751 integrally attached to the distal end 740 of the arm 720. These elastomeric flaps 751 are resiliently biased against each other when the valve is in the closed position (as shown in FIG. 12), such that they are operable to form a substantially fluid-tight seal over the opening at the distal end 740 of the arm 720.

The opposing second surface 710 of the shield 690 is attached to an insert member 715 at the distal end 760 of the insert member 715 and provides a protrusion. The insert member 715 may function as an aid for inserting and removing the cervical plug 680 from the cervical canal 759. The insert member 715 may be permanently secured to the shield 690. For instance, the cervical plug 680 may be molded as a unitary piece of material including the shield 690, arm 720, and insert member 715. Alternatively, the insert member 715 may be secured to the shield 690 with an adhesive. As illustrated in FIGS. 12-13 the insert member 715 may be secured to the shield 690 such that the insert member 715 forms a generally straight line with the arm 720. The insert member 715 may be made of a material that is at least partially translucent or transparent. Alternatively, the insert member 715 may be made of an opaque material. The insert member 715 may comprise medical-grade silicone rubber. Alternatively, the insert member 715 may be made of any suitable material including, but not limited to, plastic, glass, ceramic, metal, any type of rubber, or any combination thereof.

To facilitate removal of the cervical plug 680 after use, the insert member 715 may optionally have a string 755 attached thereto, as best seen in FIG. 13. The string 755 attaches to the cervical plug 680 via tying means through an annular cavity in the insert member 715, or alternatively, may be permanently affixed through molding means to the insert member 715. The string 755 may be a medical-grade suture, though any suitable material may be utilized. The string 755 may be of a sufficient length to extend through the vaginal canal 757 and outside of the patient's body when the cervical plug 680 is inserted in the cervical canal 753, as seen in FIGS. 19-20. By pulling the string 755, the cervical plug 680 may be removed through the vaginal canal 757 without forceps or a similar device.

Figure 14:
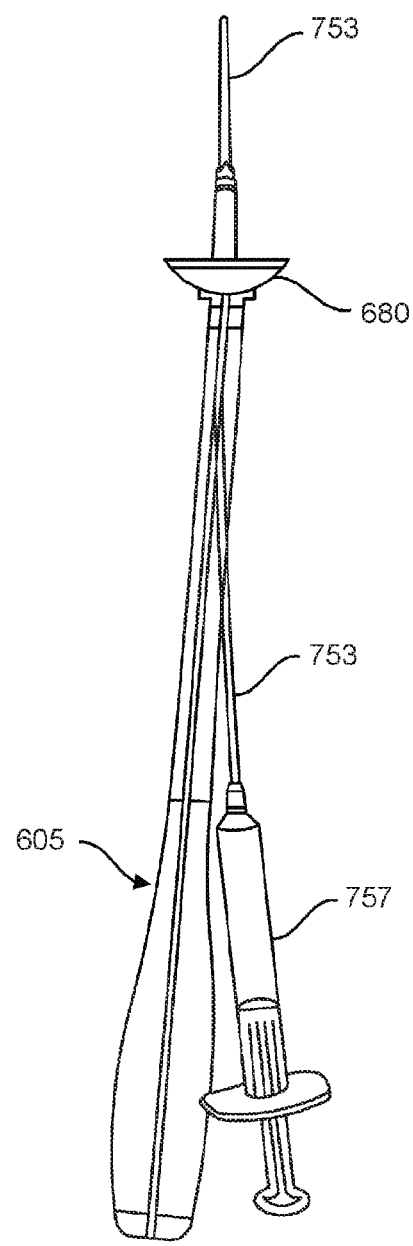
FIG. 14 is a top view of a positioning tool and a cervical plug.
Figure 15:
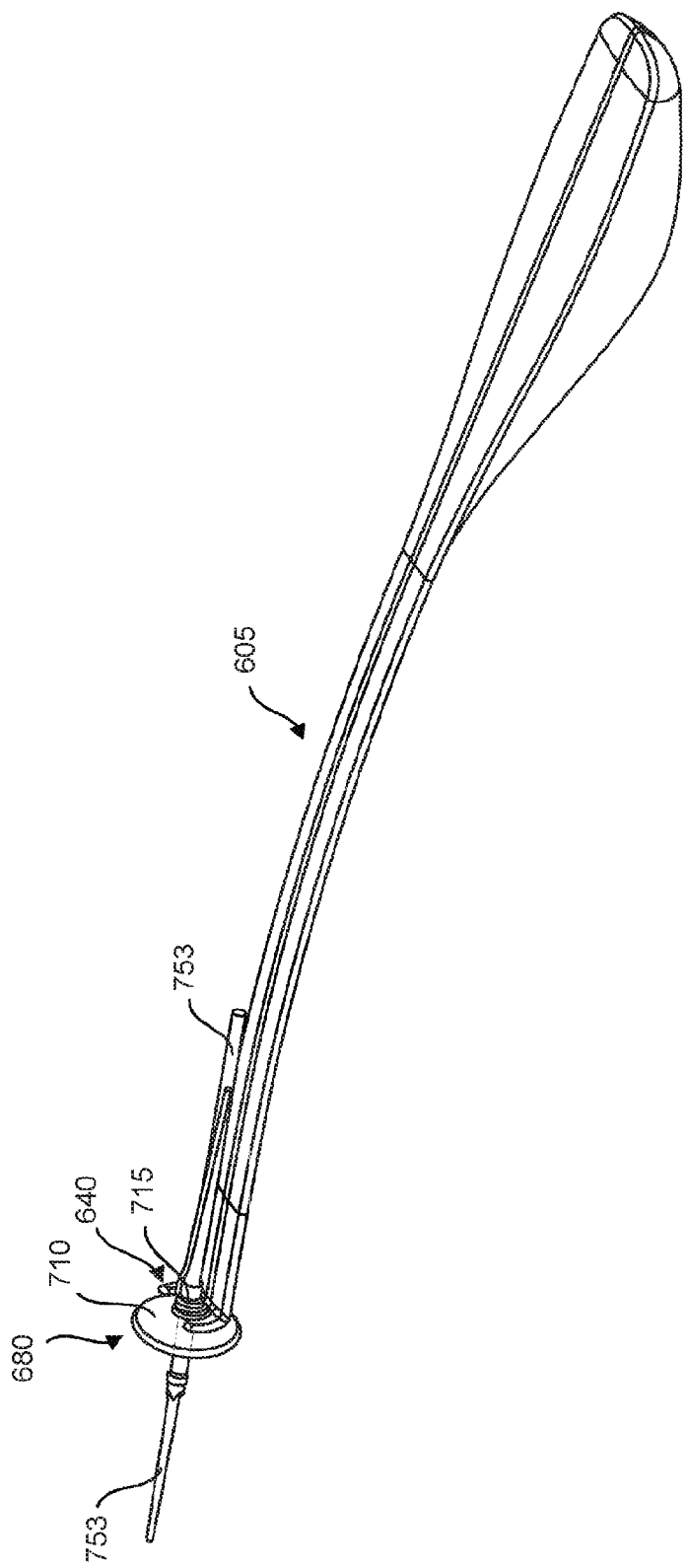
FIG. 15 is a perspective view of a positioning tool and a cervical plug with the syringe removed from the catheter.
Figure 16:
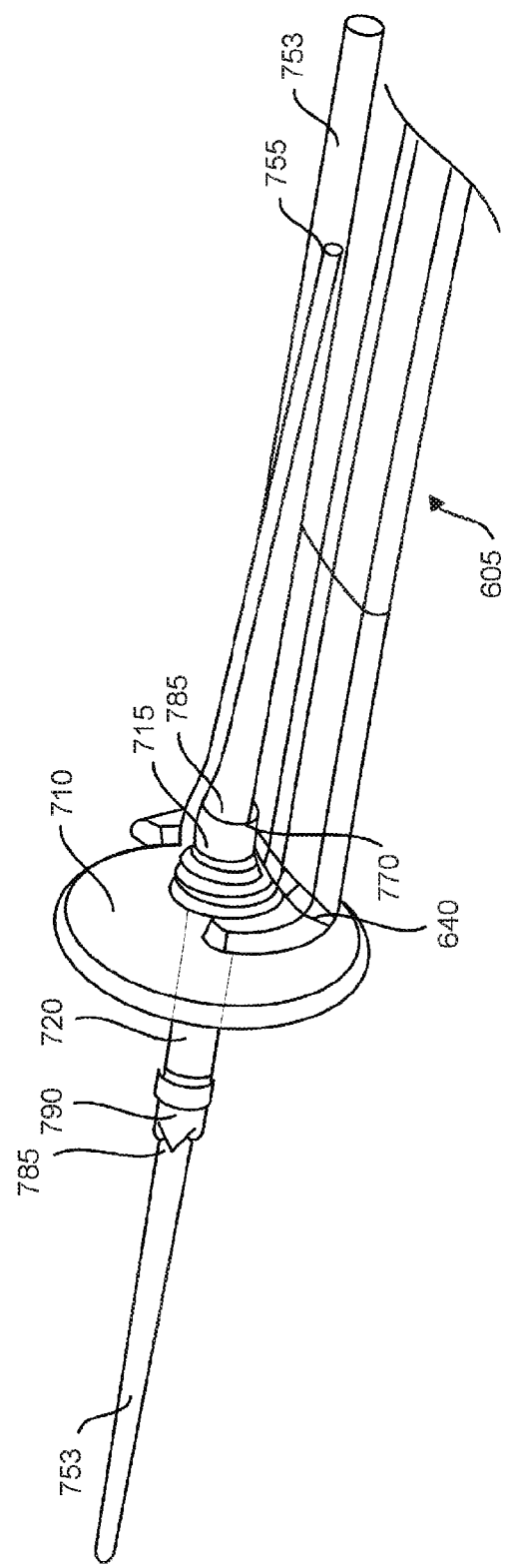
FIG. 16 is a focused perspective view of the kit shown in FIG. 15.
Figure 17:
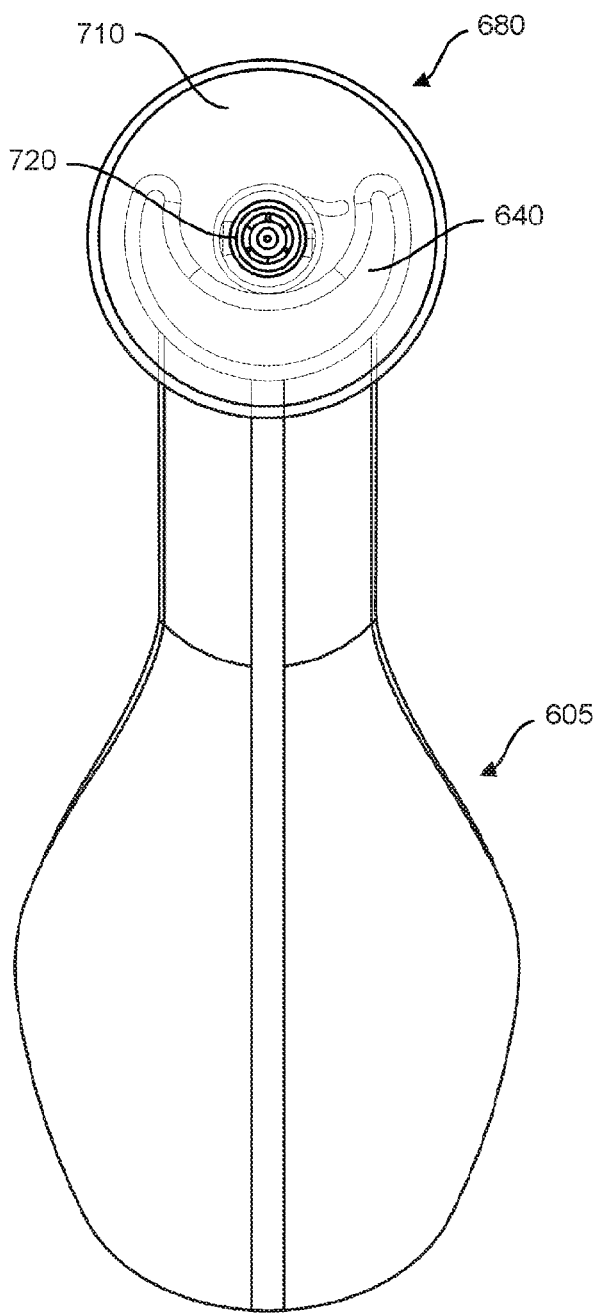
FIG. 17 is a front view of the kit shown in FIG. 15 wherein the shield of the cervical plug is translucent.
Figure 18:
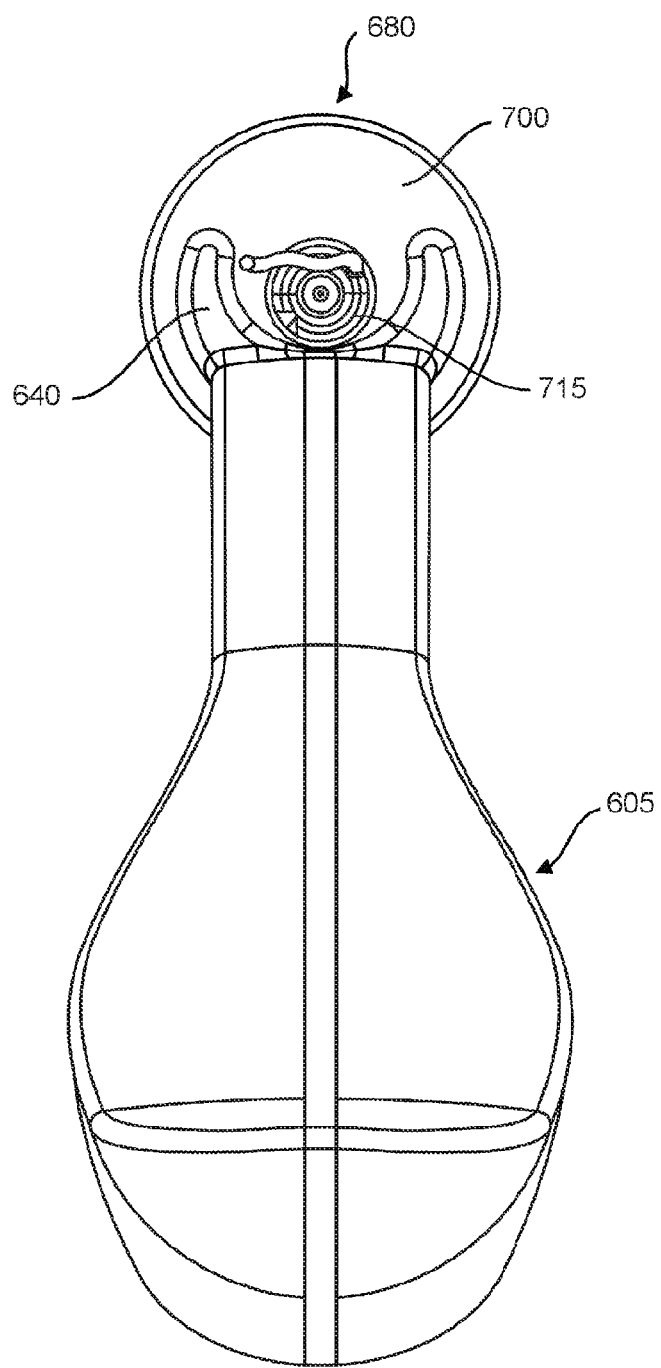
FIG. 18 is a back view of the kit shown in FIG. 15.

As shown in FIG. 14, a portion of the disclosed kit comprising the positioning tool 605, catheter 753, and cervical plug 680 is shown. As described more fully below, the catheter will be attached to a syringe 757 or some other device operable for injecting a semen deposit sample. FIGS. 15-18 closely demonstrate how the bracket 640 of the positioning tool 605 is operable to receive the insert member 715 and engage the second surface 710 of the shield 690 without interfering with the catheter 753 extending from the opening 785 at the proximal end 770 of the insert member 715.

Figure 21:
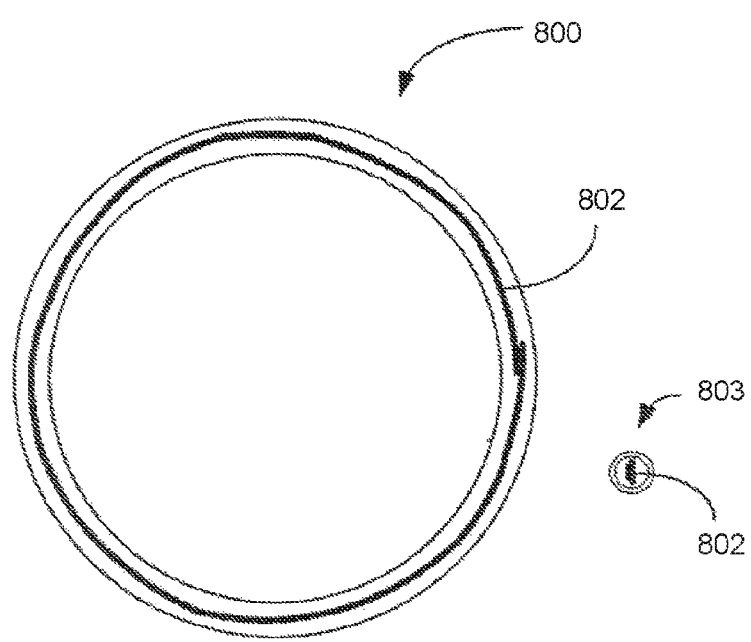
FIG. 21 is an illustration of an elastic vaginal ring with a temperature measurement and transmission arrangement.

An internal personal fertility sensor 800 is operable to identify the subtle temperature changes that occur prior to ovulation. One such device 800 for use in monitoring the ovulation of the patient is a PriyaRing™, an elastic vaginal ring temperature sensing device that can comprise an elastic ring structure and incorporated wireless transmitting arrangement 802, as illustrated in FIG. 21 and disclosed in U.S. Pat. No. 8,715,205 issued to Webster et al., the entirety of which is incorporated by reference. Cross section 803 illustrates the temperature sensing and transmission arrangement 802 can further comprise a transducer device, such as a temperature sensor, and a microcontroller, memory and wireless transmitter. Such an arrangement can incorporate a passive (battery free), battery assisted or active battery powered Radio Frequency Identification (RFID) transponder circuit with temperature measurement capability. The temperature sensing and transmission device comprises an antenna portion and electronic portion (e.g., RFID integrated circuit and other components), linked to a temperature sensing portion that can sense the surrounding temperature. The elastic ring structure can be forced in a spring-loaded state when elastically deformed thus becoming retained when disposed in a vaginal vault. In one embodiment, an active RF receiver or an RFID reader is brought in proximity to the temperature sensing and transmitting device arrangement, such as near a woman's pelvis from the outside to read the temperature and record it in a Central Processing Unit, CPU, associated with the receiver or RFID reader, such as a portable, handheld computer.

The treatment tool 810 for preparing sperm for insemination is a passive method and apparatus for filtering motile sperm from a sperm sample. The treatment tool 810 passively filters the motile sperm using a nucleopore membrane that is contained within a membrane assembly, wherein the membrane assembly is disposed in a container. In operation, a medium is placed in the container so the membrane contacts the medium. A sperm sample is placed one side of the membrane assembly, and the motile sperm migrate through the membrane leaving the non-motile sperm behind, where they can be easily extracted.

Figure 22:
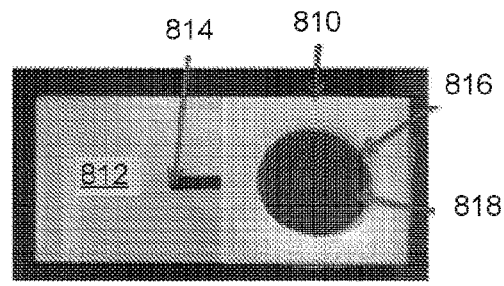
FIG. 22 is a plan view of a sperm sorting system.
Figure 23:
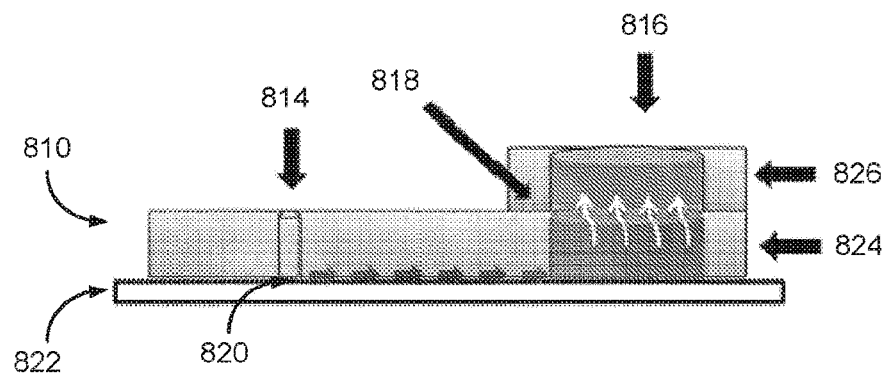
FIG. 23 is a cross-sectional view of a sperm sorting system.
Figure 24:
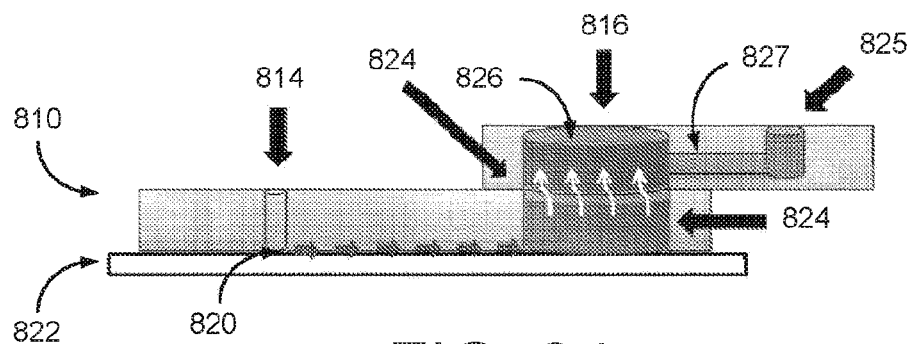
FIG. 24 is a schematic view of multichannel system with a collection chamber to concentrate the sorted sperm.

One such treatment tool 810 operable for preparing sperm for insemination into a patient is the ZyMot™, a treatment and method that integrates micro- and macro-fluidics to sort sperm in a manner that allows efficient selection of sperm that are favorably suited to fertilization, as illustrated in FIGS. 22-24, and disclosed in U.S. Pat. No. 10,422,737 issued to Demirci, et al., the entirety of which is incorporated by reference. In particular, the system recognizes that sperm suited to fertilization is most desirable and can be selected or sorted using a system presents and environment that is akin to that presented in the fertilization process. In this regard, the system is provided where macro reservoirs are connected by micropores to approximate the female genital track. The most motile, morphologically normal, mature, and functional sperm pass selectively through the micropores against gravity leaving behind dead or less functional sperm. The system is a chemical-free, centrifugation-free, and flow-free technology, where functional sperm are isolated from unprocessed semen sample with high retrieval rate.

Referring to FIG. 22, the system 810 includes a housing 812 having an inlet 814 and a collection chamber 816 having a filter 818 arranged therein. The filter 818 may be a polycarbonate filter or other filter having suitable materials properties, such as pore or passage size, as will be described. Referring to FIG. 23, the inlet 814 and collection chamber 816 are connected through a passage or flow path 820 extending along a microfluidic chip 822. As will be described, the microfluidic chip 822 may include a microchip that may be disposable and that handles unprocessed semen samples (either fresh or frozen, processed or raw), for example of 10 μl to 3 ml, and sorts sperm rapidly, such as in less than 30 minutes, without the need for complex instrumentation or trained operators.

The flow path 820 extends from the inlet 814 to the collection chamber 816. At the collection chamber 816 a first or bottom chamber 824 is located proximate to the microfluidic chip 822 and a second or top chamber 826 is located distally with respect to the microfluidic chip 822, above the first or bottom chamber 824. As will be described, the first chamber 824 is designed to collect the semen of a sample, whether fresh or frozen, processed or raw, presented to the inlet 814 and the second chamber 826 is designed to filter the motile sperms.

Referring to FIG. 24, the system 810 described above with respect to FIG. 22 may be modified to include an additional collection or concentration chamber 825 that is connected to the top chamber by a fluid connection 827. That is, in this regard, the sperm may be concentrated in the collection chamber 825 to facilitate easier harvesting.

One such tool for inducing ovulation is Ovidrel®, as disclosed in U.S. Pat. No. 5,767,251 issued to Reddy, et al., the entirety of which is incorporated by reference. This tool is biologically active heterodimeric human fertility hormones composed of two different subunits, each subunit being synthesized in the same cell transformed by at least one cell expression vector having heterologous DNA encoding each subunit with each subunit being controlled by a separate promoter. Preferred human fertility hormones include hCG, hLH and hFSH.

In accordance with one aspect of the invention, a system for sorting sperm is provided that includes a housing and a microfluidic system supported by the housing. The system also includes an inlet providing access to the microfluidic system to deliver sperm to the microfluidic system and an outlet providing access to the microfluidic system to harvest sorted sperm from the microfluidic system. The microfluidic system provides a flow path for sperm from the inlet to the outlet and includes at least one channel extending from the inlet to the outlet to allow sperm delivered to the microfluidic system through the inlet to progress along the flow path toward the outlet. The microfluidic system also includes a filter including a plurality of micropores and arranged in the flow path between the inlet and the outlet to cause sperm traveling along the flow path to move against the filter and gravity to reach the outlet.

In accordance with another aspect of the invention, a method for sorting sperm is disclosed that includes delivering a sample of sperm to an inlet connected to a microfluidic system and allowing sperm in the sample of sperm to traverse a flow path through the microfluidic system toward an outlet providing access to the microfluidic system to harvest sorted sperm from the microfluidic system. The method also includes filtering the sperm prior to reaching the outlet using a filter having a plurality of micropores and gravity to restrict movement of the sperm through the filter. The method further includes harvesting sperm passing to the outlet after passing through the filter and overcoming gravity.

For the purposes of promoting and understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the system (and components of the individual operating components of the system) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical." Numerous modifications and adaptations will be readily apparent to those skilled in this art without departing from the spirit and scope of the present invention.

The invention claimed is:

1. A method for intrauterine insemination, comprising:
    (a) self-monitoring of a menstrual cycle of a patient by said patient;
    (b) a medical practitioner making an abrasion on an endometrial lining of a uterus of the patient using an abrasion tool following menstruation by the patient;
    (c) predicting timing of ovulation by using (i) an ovulation monitoring system and/or (ii) inducing ovulation;
    (d) preparing sperm for insemination during ovulation;
    (e) guiding an intrauterine insemination catheter accompanied by a cervical plug into the patient;
    (f) positioning the cervical plug at an external os of the patient;
    (g) depositing a semen sample into a uterine cavity or a cervical canal;
    (h) removing the catheter from the patient while using a positioning tool to hold the cervical plug in place at the external os; and
    (i) leaving the cervical plug in place for a predetermined time period.

2. The method of claim 1, wherein the abrasion in step (b) is made using an abrasion tool comprising a handle, an arm, and a sleeve with an integrated cap portion, wherein the handle is attached to the arm through a connecting member having a trigger mechanism disposed therein, wherein the handle, arm, and connecting member form a single unitary body, wherein the arm further comprises an articulating tip, wherein the sleeve and cap portion are adapted to fully enclose the arm and articulating tip, wherein the trigger mechanism within said connecting member is operable to curl the articulating tip, wherein said abrasion tool is operable for making an abrasion on an endometrial lining of a uterus of a patient prior to ovulation.

3. The method of claim 1, wherein the abrasion in step (b) is made during a pre-ovulatory phase of the menstrual cycle.

4. The method of claim 3, wherein the abrasion in step (b) is made between days 7-10 of the menstrual cycle.

5. The method of claim 1, wherein the ovulation monitoring system in step (c) uses an ovulation monitoring tool operable to monitor cervical temperature to predict the timing of ovulation.

6. The method of claim 1, wherein the ovulation monitoring system in step (c) uses physician-controlled ultrasound monitoring.

7. The method of claim 1, wherein ovulation in step (c) is induced using means for stimulating follicular release.

8. The method of claim 1, wherein the sperm for insemination step (d) is prepared using a sperm treatment tool operable for filtering motile sperm from a sperm sample.

9. The method of claim 1, wherein the cervical plug in step (e) comprises an arm, a shield with a first surface and an opposing second surface, and an insert member, wherein the arm is attached to said first surface of the shield, and the insert member is attached to said second surface of the shield, wherein the first surface of the shield is operable to cover the cervical os, wherein a bore operable to receive a catheter extends longitudinally through the arm, shield, and insert member.

10. The method of claim 1, wherein the positioning tool in step (e) comprises a handle with a proximal end and a distal end, a stem extending longitudinally from the distal end of said handle and terminating at a bracket, wherein said bracket comprises a bottom segment with two spaced apart segments extending vertically from said bottom segment, wherein the tool is operable to hold the cervical plug in place while the intrauterine insemination catheter is removed, said positioning tool being configured such that it is not attached to the cervical plug and is capable of being removed from the cervical plug.

11. The method of claim 1, wherein the predetermined time period in step (g) is at between twenty minutes to two hours.

12. A method for intrauterine insemination, comprising:
a. self-monitoring of a menstrual cycle of a patient;
b. making an abrasion on an endometrial lining of a uterus following menstruation using an abrasion tool during a pre-ovulatory phase of a menstrual cycle;
c. predicting timing of ovulation using (i) an ovulation monitoring tool (ii) or inducing ovulation using means for stimulating follicular release;
d. preparing a sperm sample for insemination using a sperm treatment tool during ovulation;
e. guiding an intrauterine insemination catheter accompanied by a cervical plug into a patient's reproductive system;
f. positioning the cervical plug at an external os of the patient;
g. depositing a semen sample into a uterine cavity or a cervical canal;
h. removing the catheter from the patient while using a positioning tool to hold the cervical plug in place while the intrauterine catheter is removed;
h. removing the positioning tool; and
i. leaving the cervical plug in place for a period of between twenty minutes to two hours.

* * * * *